United States Patent
Okuda et al.

(10) Patent No.: US 6,987,273 B1
(45) Date of Patent: Jan. 17, 2006

(54) STERILIZER COMPRISING APPLICATION OF MICROWAVE

(75) Inventors: Shigeru Okuda, Sakai (JP); Kensaku Atsumi, Yawata (JP)

(73) Assignee: Matsushita Electric Works, Ltd., Osaka (JP)

( * ) Notice: Subject to any disclaimer, the term of this patent is extended or adjusted under 35 U.S.C. 154(b) by 29 days.

(21) Appl. No.: 10/416,505

(22) PCT Filed: Oct. 15, 2002

(86) PCT No.: PCT/JP02/10703

§ 371 (c)(1), (2), (4) Date: Jul. 21, 2003

(87) PCT Pub. No.: WO03/033036

PCT Pub. Date: Apr. 24, 2003

(30) Foreign Application Priority Data

Oct. 12, 2001 (JP) ........................................ 2001-315237

(51) Int. Cl.
*A61L 2/12* (2006.01)

(52) U.S. Cl. .............................. 250/455.11; 250/504 R; 422/24

(58) Field of Classification Search ............ 250/455.11, 250/504 R; 422/24
See application file for complete search history.

(56) References Cited

U.S. PATENT DOCUMENTS

| | | | |
|---|---|---|---|
| 5,166,528 A | 11/1992 | Le Vay | .................. 250/455.11 |
| 6,028,315 A | 2/2000 | Bailey et al. | |
| 6,762,414 B2 * | 7/2004 | Hur et al. | .................. 250/434 |

FOREIGN PATENT DOCUMENTS

| | | |
|---|---|---|
| JP | 2-264661 | 10/1990 |
| JP | 4-64360 | 2/1992 |
| JP | 7-248120 | 9/1995 |
| JP | 2001-145688 | 5/2001 |
| JP | 2002-191678 | 7/2002 |
| WO | 96/09842 | 4/1996 |
| WO | 97/35624 | 10/1997 |

* cited by examiner

*Primary Examiner*—Kiet T. Nguyen
(74) *Attorney, Agent, or Firm*—Greenblum & Bernstein, P.L.C.

(57) ABSTRACT

In a sterilizer for sterilizing an object to be sterilized utilizing microwaves of a microwave oven for home use, an electrodeless discharge bulb, which seals a material such as mercury which discharges owing to receiving microwaves and emitting ultraviolet rays, is fixed in an inside of a container. An object to be sterilized is held in the container in a manner so that an objective face to be sterilized of the object faces an ultraviolet ray emitting face of the electrodeless discharge bulb. In such a state, the container is put into an inside of the microwave oven, and the microwaves are irradiated, so that the ultraviolet rays emitted from the electrodeless discharge bulb are irradiated to the objective face of the object for processing the serialization.

18 Claims, 20 Drawing Sheets

STERILIZER COMPRISING APPLICATION OF MICROWAVE

TECHNICAL FIELD

The present invention relates to a sterilizer for sterilizing an object to be sterilized owing to ultraviolet rays with using a microwave generator such as a microwave oven for home use.

BACKGROUND ART

A sterilizer for sterilizing an object to be sterilized is conventionally proposed, in which ultraviolet rays are emitted from low-pressure mercury vapor by irradiating microwaves, and the ultraviolet rays are further irradiated to the object to be sterilized for processing the serialization.

FIG. 24 shows a sterilizing method for medical implements (first prior art) shown in, for example, Publication Gazette of Japanese Patent Application 2001-145688. Since the medical implements are generally made of metals, the medical implements cannot directly be put into an inside of a microwave generator such as a microwave oven. Thus, a glass bulb 152 into which low-pressure mercury vapor is enclosed and objects 153 to be sterilized are disposed in a container 151 which is filled by water, and the container 151 is put into an inside of a microwave oven 150. Then, microwaves are generated by activating the microwave oven 150, and the microwaves are irradiated to the bulb 152. Mercury vapor in the bulb 152 is excited by energy of the microwaves, and ultraviolet rays having a predetermined wavelength are emitted, so that the objects 153 are sterilized owing to the ultraviolet rays. In FIG. 24, numerals 154 designate ventilation openings provided on a housing of the microwave oven 150.

FIG. 25 shows a sterilizing method of containers such as glass bottles (second prior art) shown in, for example, Publication Gazette of Japanese Patent Application 10-502563 (corresponding to WO96/09842). Under a condition that a narrow glass bulb 156, into which low-pressure mercury vapor is enclosed, is suspended in an inside of an object 157 to be sterilized, the object 157 with the bulb 156 is put into an inside of a microwave generator 158. Then, microwaves are irradiated for emitting ultraviolet rays, so that inner faces of the object 157 are sterilized. In FIG. 25, numerals 159 designate energies of microwaves, and numerals 160 designate energies of ultraviolet rays.

FIG. 26 shows a sterilizing method of contact lenses (third prior art) shown in, for example, Publication Gazette of Japanese Patent Application 2000-507140 (corresponding to WO97/35624). A container 162A and a cap 162B are respectively formed midair by glass or the like, and low-pressure mercury vapor is enclosed into midair portions of them. Under a condition that objects 163 are contained in the inside of the container 162A and the cap 162B is fitted to the container 162, the container 162A with the cap 162B is put into an inside of a microwave generator 164. Then, microwaves are irradiated for irradiating ultraviolet rays to the objects 163 from the container 162A and the cap 162B, so that sterilizing of the objects is processed.

In the above-mentioned first prior art, since the bulb 152 and the objects 153 are send on the bottom of the container 151 filled by water, the ultraviolet rays emitted from the bulb 153 are not necessarily irradiated to whole of the objects 153 evenly. Thus, there is a possibility that sterilized portions and not sterilized portions are generated on the object 153. Furthermore, since the relative positional relationship between the bulb 152 and each of the objects 153 is instable, when a table of the microwave oven 150 rotates, the positional relationship between the bulb 152 and the object 153 varies. Thus, there is a possibility that sufficient serialization effect cannot be obtained.

The above-mentioned second prior art relates to the serialization procedure of the returnable bottles, which needs a dedicated apparatus used in a supplier refilling the contents of the bottle, so that it is not suitable for sterilizing the container readily in the home. Furthermore, when there is convex and concave structure on inner faces of the container like the wine bottle, the ultraviolet rays cannot be irradiated to shaded portion due to the convex and concave structure, so that the serialization procedure may be incomplete.

In the above-mentioned third prior art, since the container 162A and the cap 162B themselves have bulb function for emitting the ultraviolet rays, the structures of the container 162A and the cap 162B become complex and the manufacturing costs of them become higher. Furthermore, since the container 162A and the cap 162B are the glass midair body and strengths of them are lower to be easily broken, they require careful handling.

When the microwave oven for home use is used as the microwave generator, the ultraviolet rays are leaked to outside of the microwave oven through the ventilation openings (see numerals 154 in FIG. 24), so that there is a fear that the ultraviolet rays damages eyes of a user who processes the serialization of the objects.

DISCLOSURE OF INVENTION

An object of the present invention is to provide a sterilizer which enables the serialization of the objects to be sterilized readily with using the microwave oven which is generally used in the home.

For accomplishing the above-mentioned purpose, a sterilizer in accordance with an aspect of the present invention sterilizes an objective face of an object to be sterilized owing to irradiating ultraviolet rays to the objective faces, and comprises an electrodeless discharge bulb containing a material emitting the ultraviolet rays when it receives energy of microwaves, a bulb stand for supporting the bulb, and a holder for holding the object in a manner so that the objective face of the object faces an ultraviolet ray emitting face of the bulb.

By such a configuration, the object to be sterilized can readily be sterilized by putting the object with the bulb in an inside of a microwave generator such as a microwave oven in home use under a condition that the object is held on the holder. Furthermore, the relative positional relationship between the bulb and the object is defined by the bulb stand and the holder, so that the positional relation between the bulb and the object will never be varied even when vibrations due to rotation of a table of the microwave oven are applied. Thus, the user inexperience in the treatment of the sterilizer can readily and surely sterilize the object.

BEST MODE FOR CARRYING OUT THE INVENTION

First Embodiment

Figure 1:
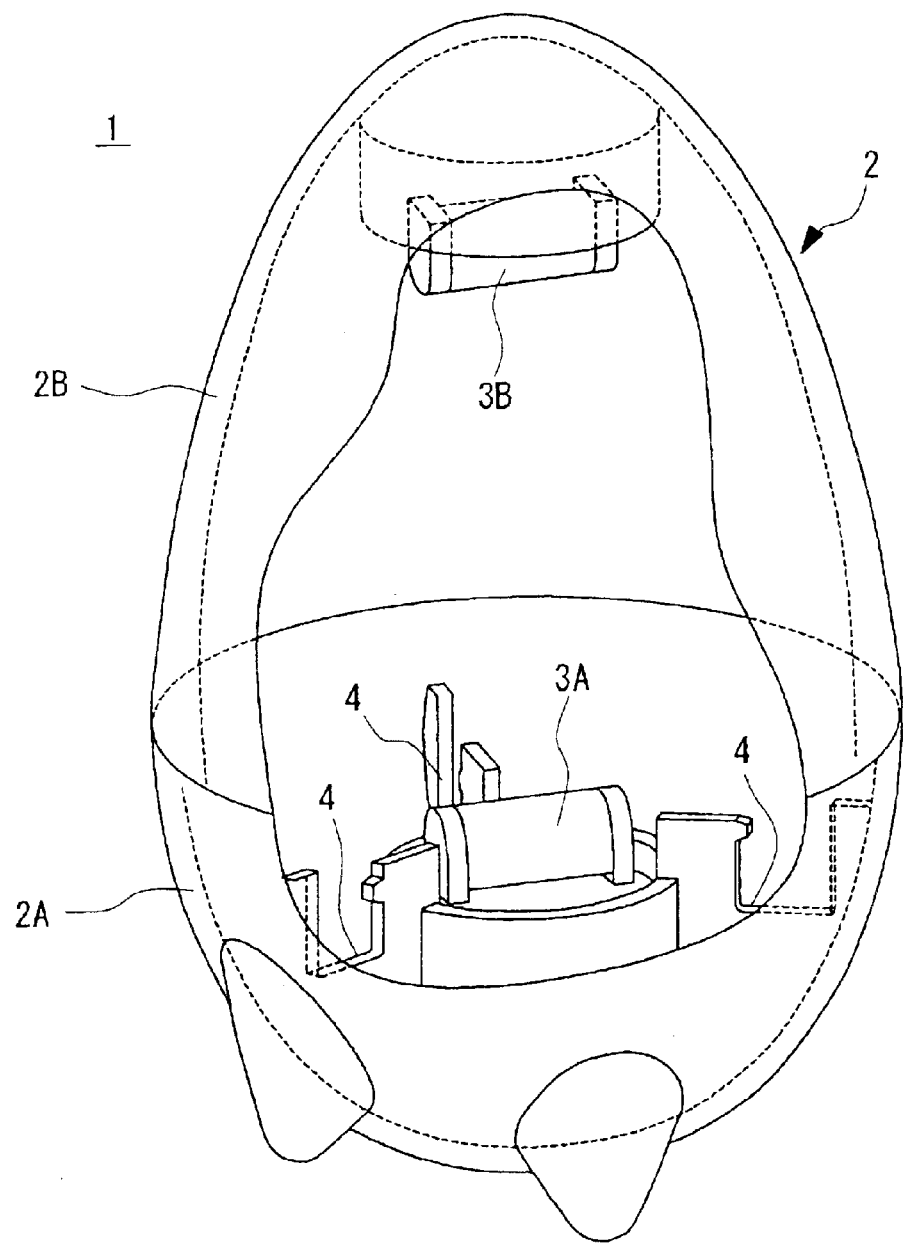
FIG. 1 is a perspective view showing a configuration of a sterilizer in a first embodiment of the present invention.
Figure 2:
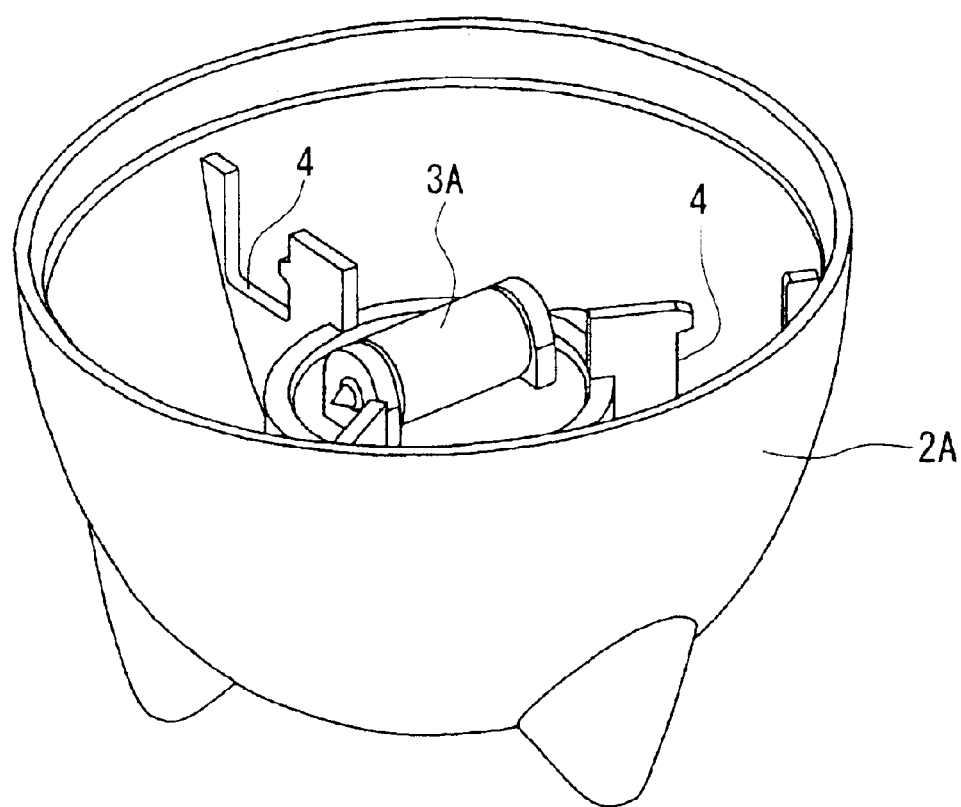
FIG. 2 is a perspective view showing a configuration of a base member of the sterilizer in the first embodiment.
Figure 3:
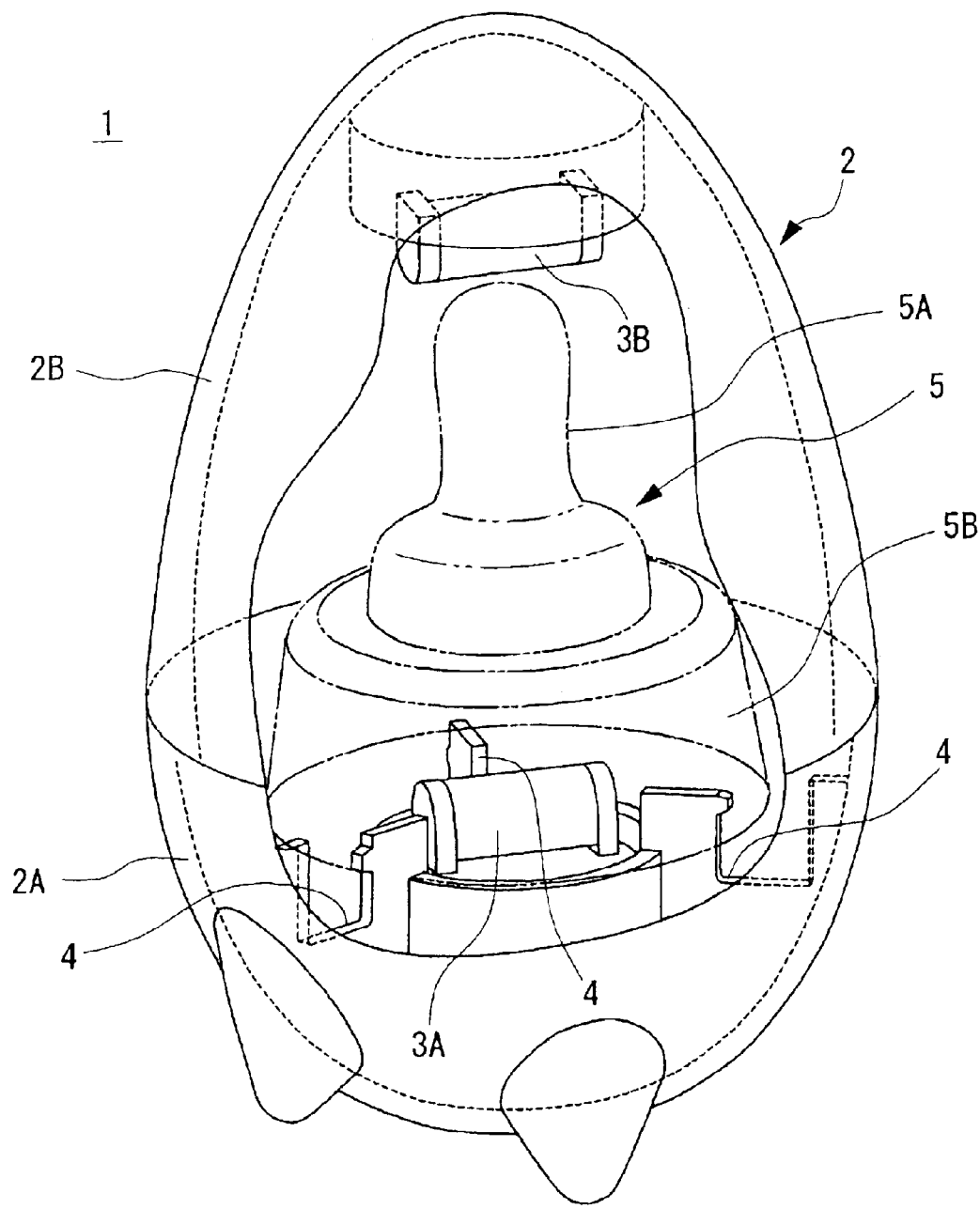
FIG. 3 is a perspective view showing a condition that an object to be sterilized is contained in the sterilizer in the first embodiment.
Figure 4:
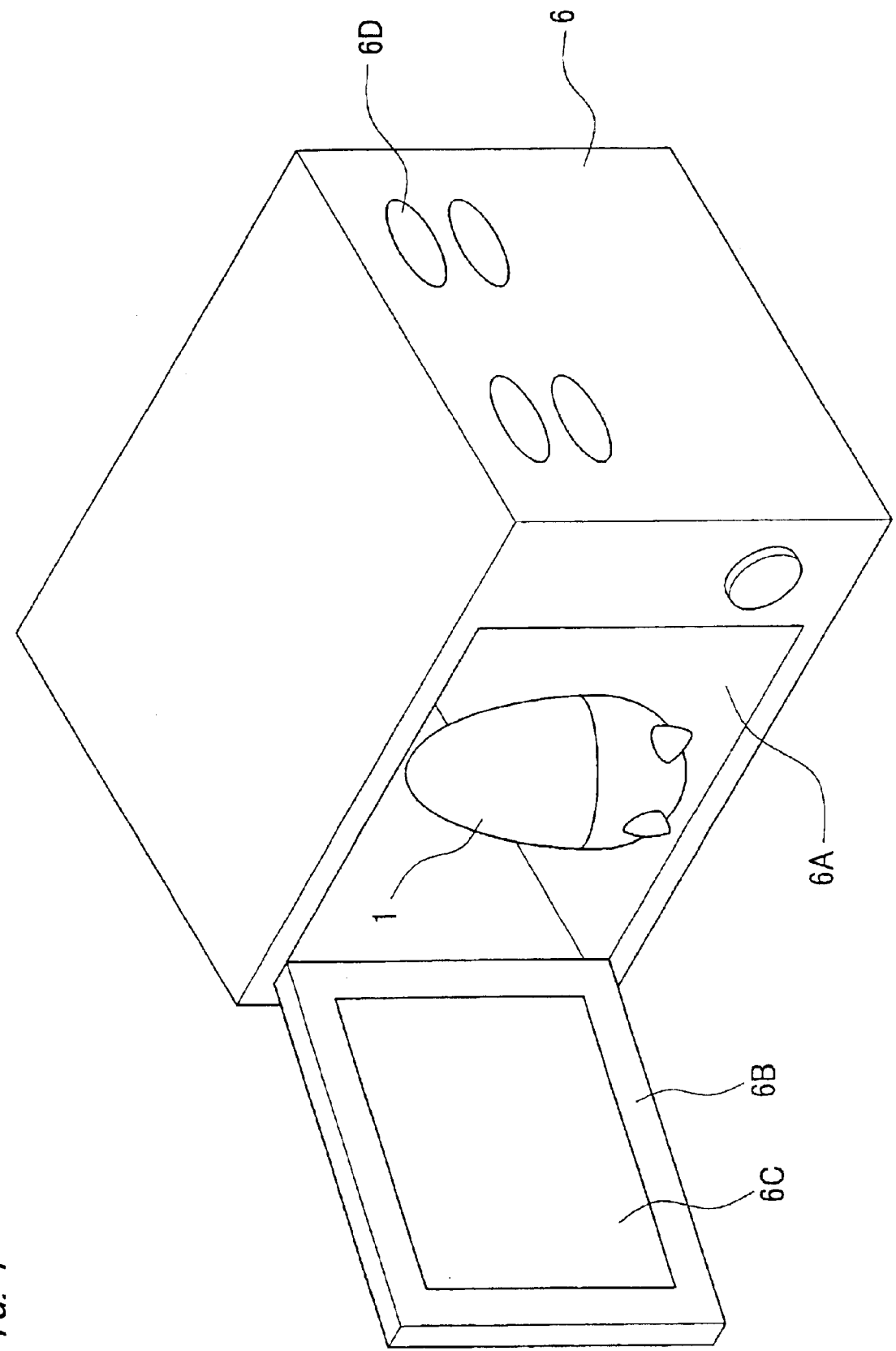
FIG. 4 is a perspective view showing a condition that the sterilizer is put into a microwave oven for processing the serialization in the first embodiment.

A first embodiment of the present invention is described. FIG. 1 is a perspective view showing a configuration of a sterilizer 1 in the first embodiment. FIG. 2 is a perspective view showing a configuration of a base member 2A of the sterilizer 1. FIG. 3 is a perspective view showing a condition that an object 5 to be sterilized is contained in the sterilizer 1. FIG. 4 is a perspective view showing a condition that the sterilizer 1 is put into a microwave oven 6 when the serialization is processed.

As shown in the figures, the sterilizer 1 is configured by a container 2 having an egg shaped cross section in a longitudinal direction and a circular cross section in a lateral direction, and dividable into a base member 2A and a cover member 2B, and a first electrodeless discharge bulb 3A and a second electrodeless discharge bulb 3B which are provided in an inside of the container 2, and so on. In the following description, the "electrodeless discharge bulb" is simply abbreviated as "bulb".

The first bulb 3A is fixed substantially at the center of the base member 2A, and a holder 4 for holding an object to be sterilized is formed around the first bulb 3A. The second bulb 3B is fixed substantially at the center of the cover member 2B. The first bulb 3A and the second bulb 3B are respectively formed by enclosing a material emitting ultraviolet rays such as mercury vapor in a tubular glass bulb, and fixed in a manner so that the ultraviolet rays emitted from mercury molecules which are excited by receiving electric field energy of microwaves are irradiated toward the inside of the container 2.

The base member 2A and the cover member 2B, which constitute the container 2, are respectively made of a material such as a fluoroplastic which transmits the microwaves but the ultraviolet rays. Furthermore, it is preferable that at least a material of the cover member 2B can transmit visible rays. Still furthermore, it is preferable that a fluorescent material is spread on at least a part of inner faces or outer faces of the base member 2A and the cover member 2B or the fluorescent material is mixed into the materials of the base member 2A and the cover member 2B.

In FIG. 3, a teat 5A of a baby's bottle and a screw 5B for fixing the teat 5A on the bottle are illustrated as examples of the objects 5 to be sterilized. The sterilizer 1 can be used for any goods which need the serialization, so that the kinds of the objects 5 are not limited.

Subsequently, the method for using the sterilizer 1 is described. The teat 5A is mounted on the screw 5B which are previously washed by washing preparation, and the screw 5B is disposed on the holder 4 of the base member 2 in a manner so that an inner periphery of the screw 5B is engaged with projections formed on the holder 4. After that, the cover member 2B is engaged with the base member 2A. Therefore, as shown in FIG. 3, the first bulb 3A on the base member 2A faces the inner faces of the objects 5, and the second bulb 3B on the cover member 2B faces the outer faces of the objects 5.

Under such the condition, as shown in FIG. 4, the sterilizer 1 is put into an inside 6A of a microwave oven (microwave generator) 6. After closing a door 6B, the microwave oven 6 is activated for irradiating the microwaves.

The microwaves reach to the first bulb 3A through not only the container 2 (base member 2A and cover member 2B) of the sterilizer 1 but also the objects 5 (teat 5A and screw 5B). Furthermore, the microwaves reach to the second bulb 3B through the container 2 (base member 2A and cover member 2B) of the sterilizer 1.

The microwaves reach to the first bulb 3A and the second bulb 3B excite mercury molecules in the insides of the first bulb 3A and the second bulb 3B, and ultraviolet rays are emitted from the excited mercury molecules. Furthermore, the ultraviolet rays are emitted outwardly through the glass bulbs of the first bulb 3A and the second bulb 3B, and are irradiated to the inner faces and the outer faces of the objects 5. The ultraviolet rays have, for example, a wavelength of 254 nm with sterilizing effect, so that the inner faces and the outer faces of the objects 5 are sterilized. Furthermore, ozone gas is generated by the ultraviolet rays emitted from the first bulb 3A and the second bulb 3B, and the ozone gas is enclosed in the inside of the container 2, so that the serialization owing to the ozone gas can be processed simultaneously.

Since the sterilizer 1 in the first embodiment can readily sterilize the object, especially, with using the microwave oven for home use, it can be used for sterilizing objects such as a pacifier, toys and so on which are put into baby's mouth, further to the above-mentioned teat and screw of the baby's bottle.

Generally, there are many types of the microwave oven for home use in which the table is rotated. However, in the sterilizer 1 in the first embodiment, the first bulb 3A and the second bulb 3B are respectively fixed on the base member 2A and the cover member 2B constituting the container 2, and the objects 5 are held on the holder 4 of the base member 2A, so that relative positional relationships between the objects 5 and the first bulb 3A and the second bulb 3B are never varied even when the vibrations due to the rotation of the table are applied. Thus, the serialization of the objects 5 can be processed stably.

Furthermore, since the base member 2A and the cover member 2B constituting the container 2 are made of the material transmitting no ultraviolet ray, the ultraviolet rays emitted from the first bulb 3A and the second bulb 3B are never leaked to the outside of the container 2. Thus, no ultraviolet ray will be leaked from a window 6C or ventilation openings 6D of the microwave oven 6. Accordingly, when a user carries out another operation in the vicinity of the microwave oven while the objects are sterilized with using the sterilizer 1, the ultraviolet rays never come into the user's eyes erroneously, so that the ultraviolet rays causes no harm.

Furthermore, owing to spreading the fluorescent material on the inner faces or the outer faces of the base member 2A and/or the cover member 2B, alternatively, owing to mixing the fluorescent material into the material of the base member 2A and/or the cover member 2B, the visible rays are emitted from the fluorescent material when the ultraviolet rays are emitted from the first bulb 3A and the second bulb 3B. Thus, when at least the cover member 2B of the container 2 is made, for example, clear and colorless so as to transmit the visible rays, the user can recognize that the serialization is processed owing to the ultraviolet rays by observing the visible rays transmitting through the cover member 2. Furthermore, by observing the brightness of the visible rays transmitting through the cover member 2B, it is possible to find the deterioration of the first bulb 3A and the second bulb 3B when the brightness of the visible rays is reduced.

Still furthermore, when the seal-up of the container 2 is maintained after the serialization owing to the ultraviolet rays is over, the serialization owing to the ozone gas sealed in the inside of the container 2 can be maintained.

Still furthermore, in the first embodiment, the object 5 can be dismounted from the holder 4 of the base member 2 by nipping the screw 5B when the sterilized objects 5 are dismounted from the container 2, so that the possibility to touch the teat 5A, which is directly put into baby's mouth, can be reduced. It is needless to say that the height of side walls of the base member 2A and the shapes of the holder 4 are designed so that the sterilized objects 5 can easily be dismounted.

Second Embodiment

Figure 5:
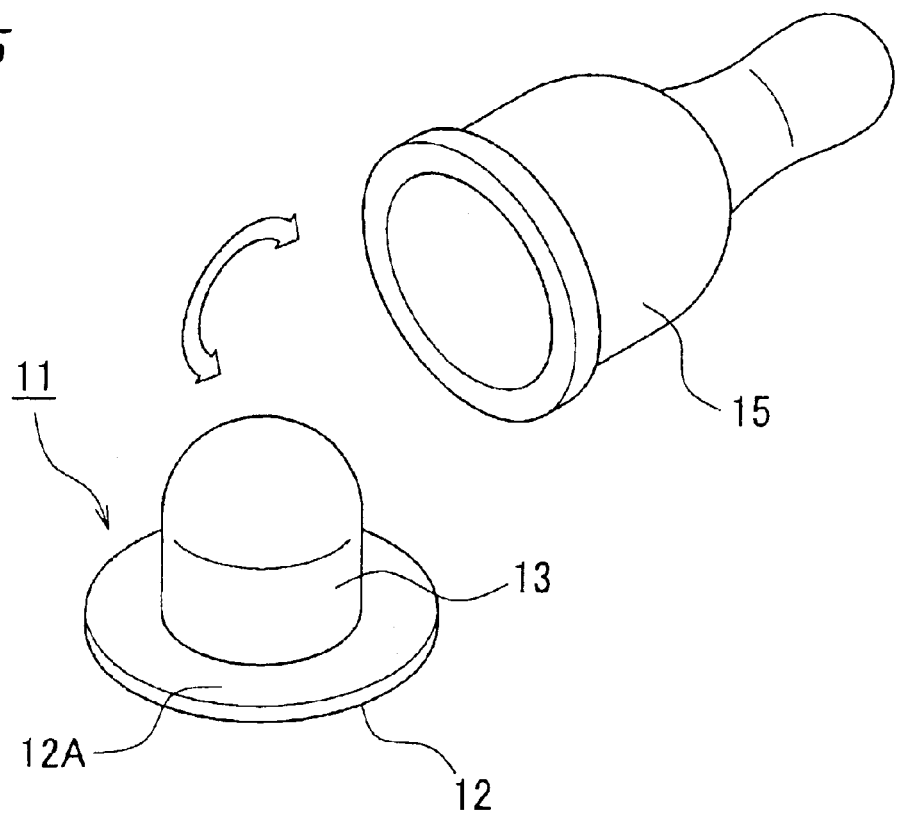
FIG. 5 is a perspective view showing a configuration of a sterilizer in a second embodiment of the present invention.
Figure 6:
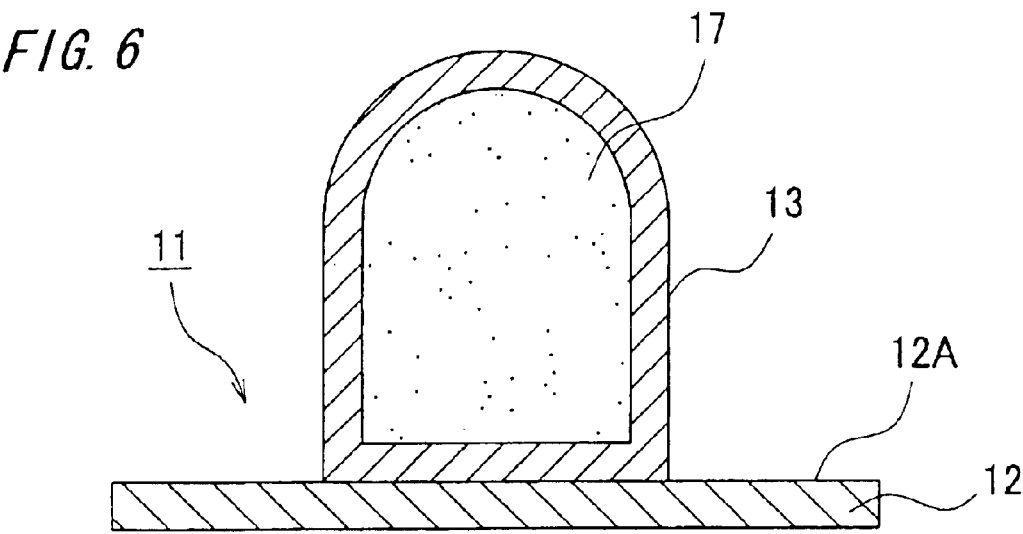
FIG. 6 is a sectional view showing the configuration of the sterilizer in the second embodiment.
Figure 7:
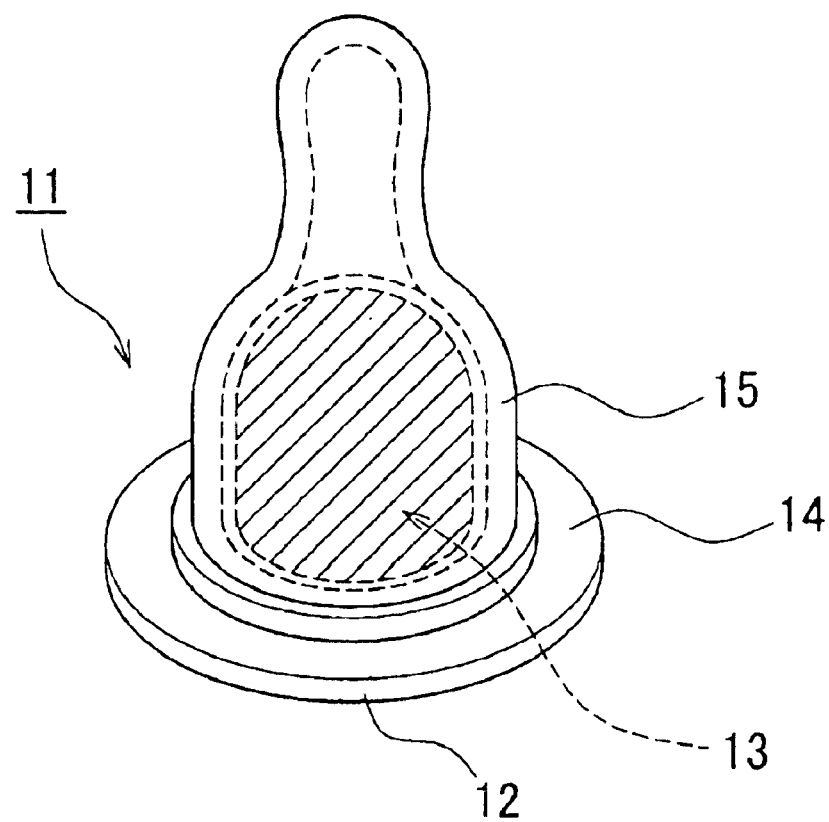
FIG. 7 is a perspective view showing a condition that an object to be sterilized is laid on the sterilizer in the second embodiment.
Figure 8:
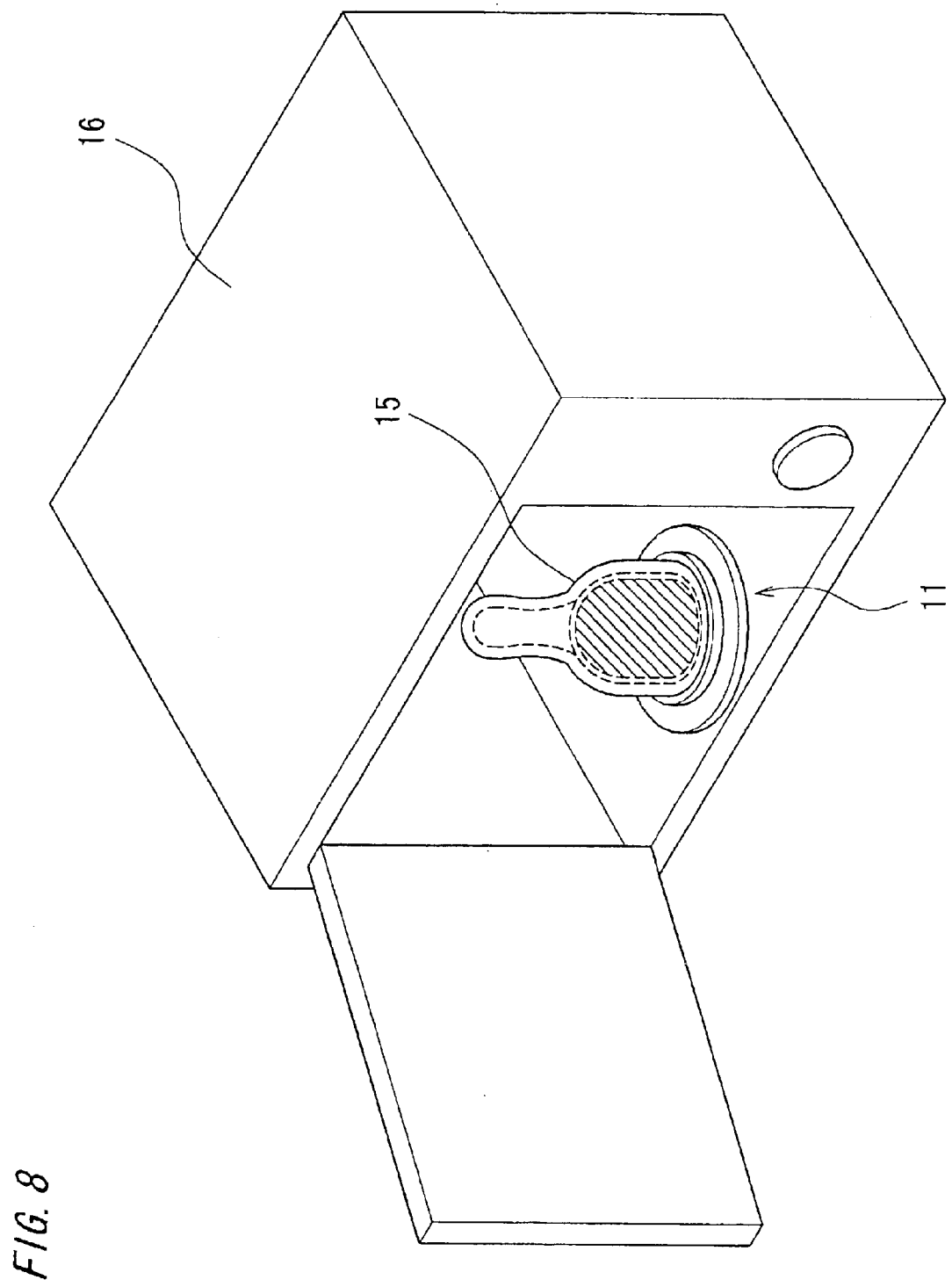
FIG. 8 is a perspective view showing a condition that the sterilizer is put into the microwave oven for processing the serialization in the second embodiment.

A second embodiment of the present invention is described with reference to the drawings. FIG. 5 is a perspective view showing a configuration of a sterilizer 11 in the second embodiment. FIG. 6 is a sectional view showing the configuration of the sterilizer 11. FIG. 7 is a perspective view showing a condition that an object 15 to be sterilized is held on the sterilizer 11. FIG. 8 is a perspective view showing a condition that the sterilizer 11 is put into a microwave oven 16 when the serialization is processed.

As can be seen from the figures, the sterilized 11 in the second embodiment is configured by a disc shaped holder 12, a substantially bell shaped bulb 13 which is fixed at the center of the holder 12, and so on. The sterilizer 11 is used in a manner so that the object 15 is directly laid over the bulb 13. The holder 12 serves as both of the bulb stand for supporting the bulb 13 and the holder for holding the object 15.

By forming a flange portion 12A of an upper face of the holder 12 outwardly from the bulb 13 wider, the sterilizer 11 can be treated with handling the flange portion 12A. Thus, it is possible to reduce the fear to pollute the object 15 while the sterilized object 15 is treated.

Similar to the above-mentioned first embodiment, the bulb 13 is formed that mercury vapor is enclosed in an inside of a midair glass container. A teat of a baby bottle is illustrated as an example of the object 15. It is needless to say that the object to be sterilized is not restricted by the illustration.

In the second embodiment, at least a part of exterior of the bulb 13 is configured to take along at least a part of inner faces of the object 15. Thus, the relative positional relationship between the bulb 13 and the object 15 can be made stable with using no container. As a result, unevenness of serialization effect due to vibrations of rotation of a table of the microwave oven 16 can be prevented.

Furthermore, by forming at least a part of the shapes and dimensions of the bulb 13 to have a predetermined relation (for example, similar figure) with respect to a part of the shapes and dimensions of the object 15, a distance between the bulb 13 and an objective face (inner face in this case) of the object 15 can be made much shorter and substantially constant, even though the versatility will be reduced. Thus, the ultraviolet rays emitted from the bulb 13 can effectively be irradiated to the objective face of the object 15. Furthermore, a part of the bulb 13 can contact with the objective face (inner face) of the object 15. Still furthermore, since the shape of the bulb 13 is not restricted to the bell shape, it is possible to have another shape such as cylindrical shape.

In the second embodiment, the ultraviolet rays are mainly irradiated to the inner faces of the object 15, and the outer faces are sterilized owing to the ultraviolet rays transmitted through the object 15, so that the same serialization effect as that on the inner faces cannot necessarily be obtained on the outer faces. It, however, is effective that at least the inner faces, which are difficult to be washed by the washing preparation, can be sterilized owing to the ultraviolet rays, effectively.

Third Embodiment

Figure 9:
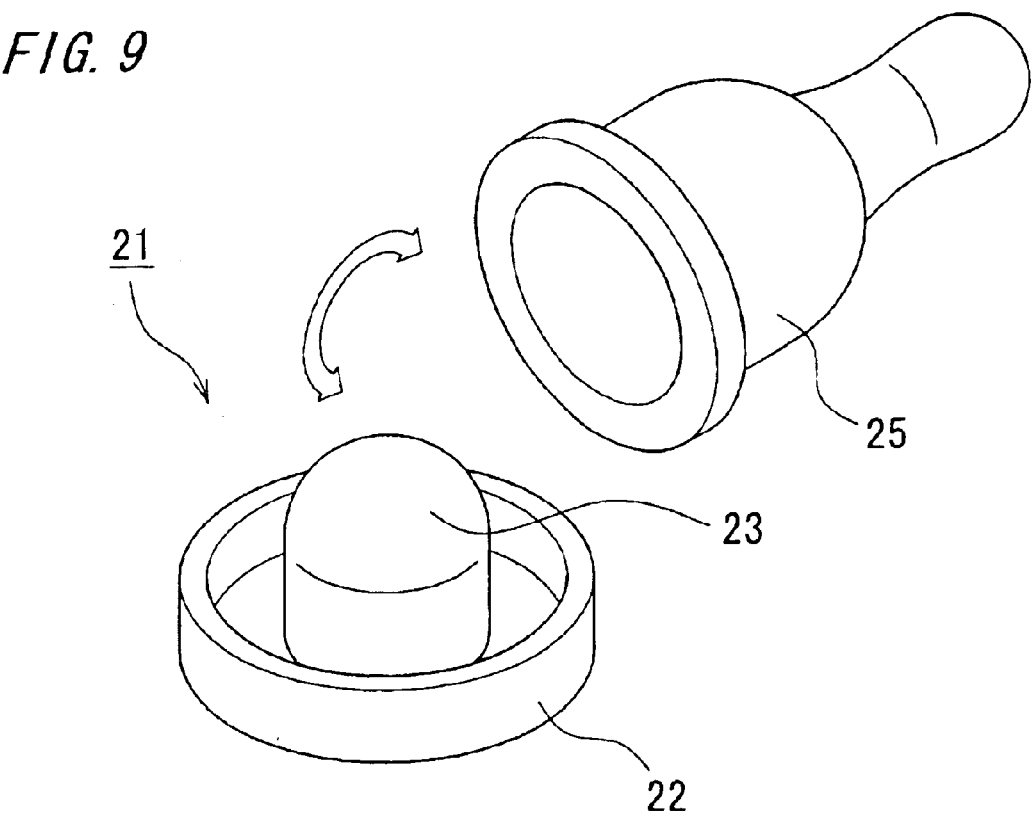
FIG. 9 is a perspective view showing a configuration of a sterilizer in a third embodiment of the present invention.
Figure 10:
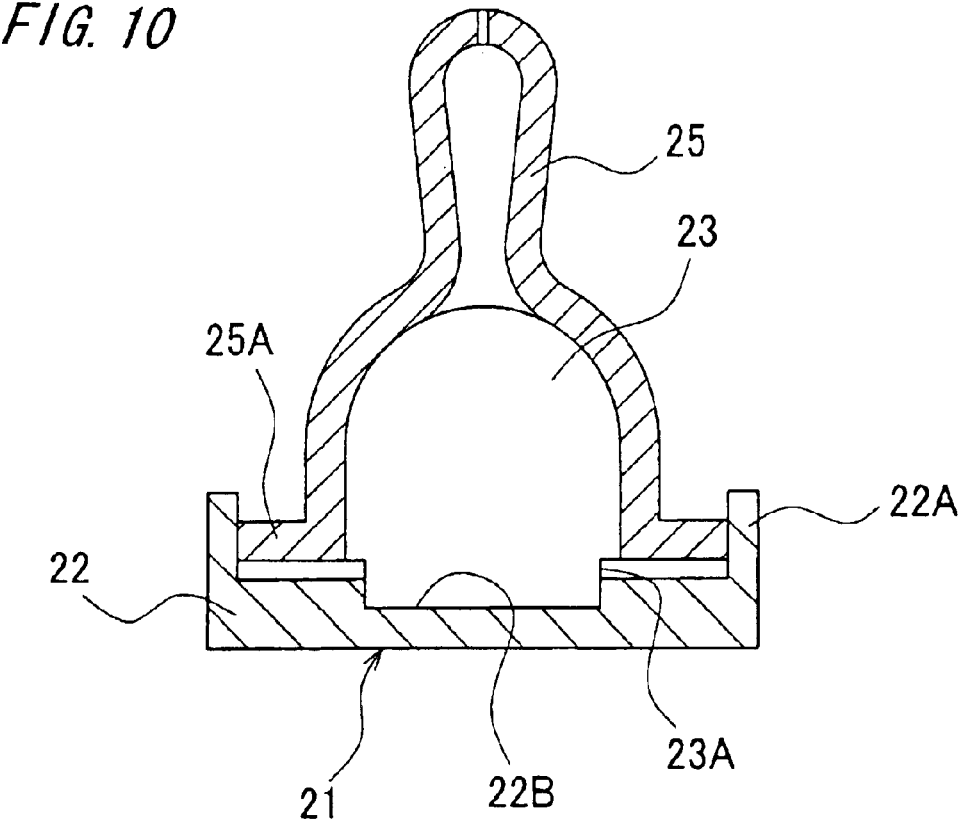
FIG. 10 is a sectional view showing a condition that an object to be sterilized is laid on the sterilizer in the second embodiment.

A third embodiment of the present invention is described. FIG. 9 is a perspective view showing a configuration of a sterilizer 21 in the third embodiment. FIG. 10 is a sectional view showing a condition that an object 25 to be sterilized is held on the sterilizer 21.

As can be seen from figures, the third embodiment is substantially a modification of the above-mentioned second embodiment, in which a tray 22 with a perpendicular wall 22A is used as a holder of an object 25 instead of the disc shaped holder. An inner diameter of the perpendicular wall 22A of the tray 22 is designed substantially the same as or a little larger that an external diameter of a bottom 25A of the object 25. Thus, there is rarely a brattle between the tray 22 and the object 25 when the object 25 is held on the sterilizer 21. As a result, the relative positional relationship between the bulb 23 and the object 25 can be made stable, and a distance between the bulb 23 and the object 25 can be made much shorter and substantially constant. Thus, the ultraviolet rays emitted from the bulb 23 can effectively be irradiated to the objective face of the object 25.

Furthermore, a fitting portion 22B is formed at the center of the tray 22, so that a bottom 23A of the bulb 23 can be fitted thereto. That is, the bulb 23 is detachable from the tray 22. Accordingly, the sterilizer 21 can be washed with discomposing to the tray 22 and the bulb 23.

The figures illustrate an example of the perpendicular wall 22A which is formed along whole of the circumference of the tray 22. It, however, is not restricted to the illustration, so that it is possible to provide the perpendicular wall partially. Other configuration and effects are similar to those in the above-mentioned second embodiment, so that the explanations of them are omitted.

Fourth Embodiment

Figure 11:
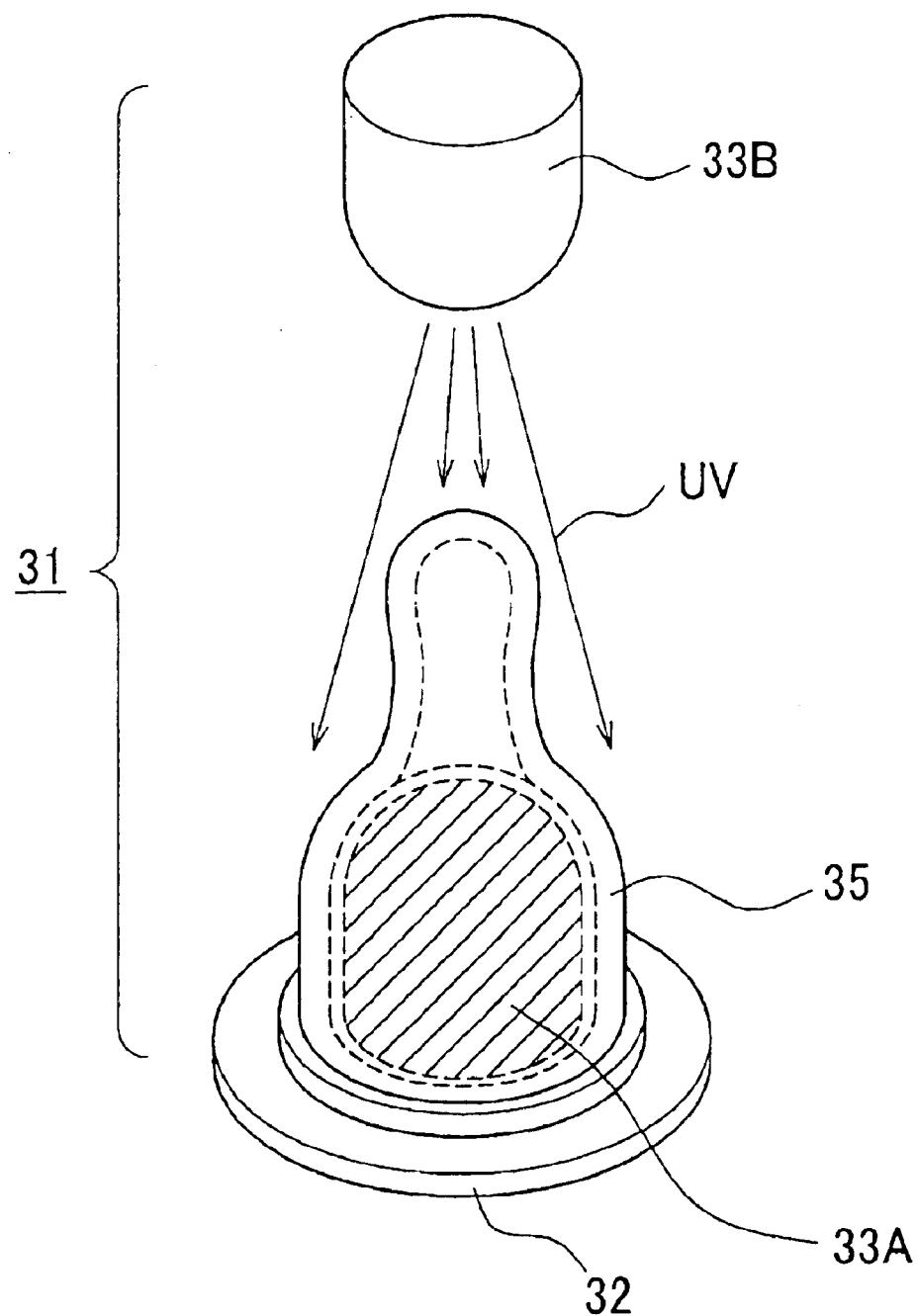
FIG. 11 is a perspective view showing a configuration of a sterilizer in a fourth embodiment of the present invention.

A fourth embodiment of the present invention is described. FIG. 11 is a perspective view showing a configuration of a sterilizer 31 in the fourth embodiment.

The sterilizer 31 is configured by a disc shaped holder 32, a substantially bell shaped first bulb 33A fixed at the center of the holder 32, a second bulb 33B provided for facing the first bulb 33A, which is used in a manner so that an object 35 is directly laid over the first bulb 33A. In comparison with the second embodiment shown in FIG. 5, it is different that the second bulb 33B is provided for irradiating the ultraviolet rays to outer faces of the object 35.

It is possible that the second bulb 33B has alternative of the same shape as and a different shape from that of the first bulb 33A. Furthermore, it is possible that a stand is used for supporting the second bulb 33B for facing the first bulb 33A. Alternatively, a magnet can be used for fixing the second bulb 33B on a ceiling of a cooking space of a microwave oven. Still furthermore, it is possible to use a plurality of second bulbs 33B for irradiating the ultraviolet rays to the outer faces of the object 35 evenly.

According to the fourth embodiment, the ultraviolet rays can be irradiated to both of the inner faces and the outer faces of the object 35 further to the effects of the above-mentioned second embodiment, so that the inner faces and the outer faces of the object 35 can be sterilized substantially at the same level.

Figure 12:
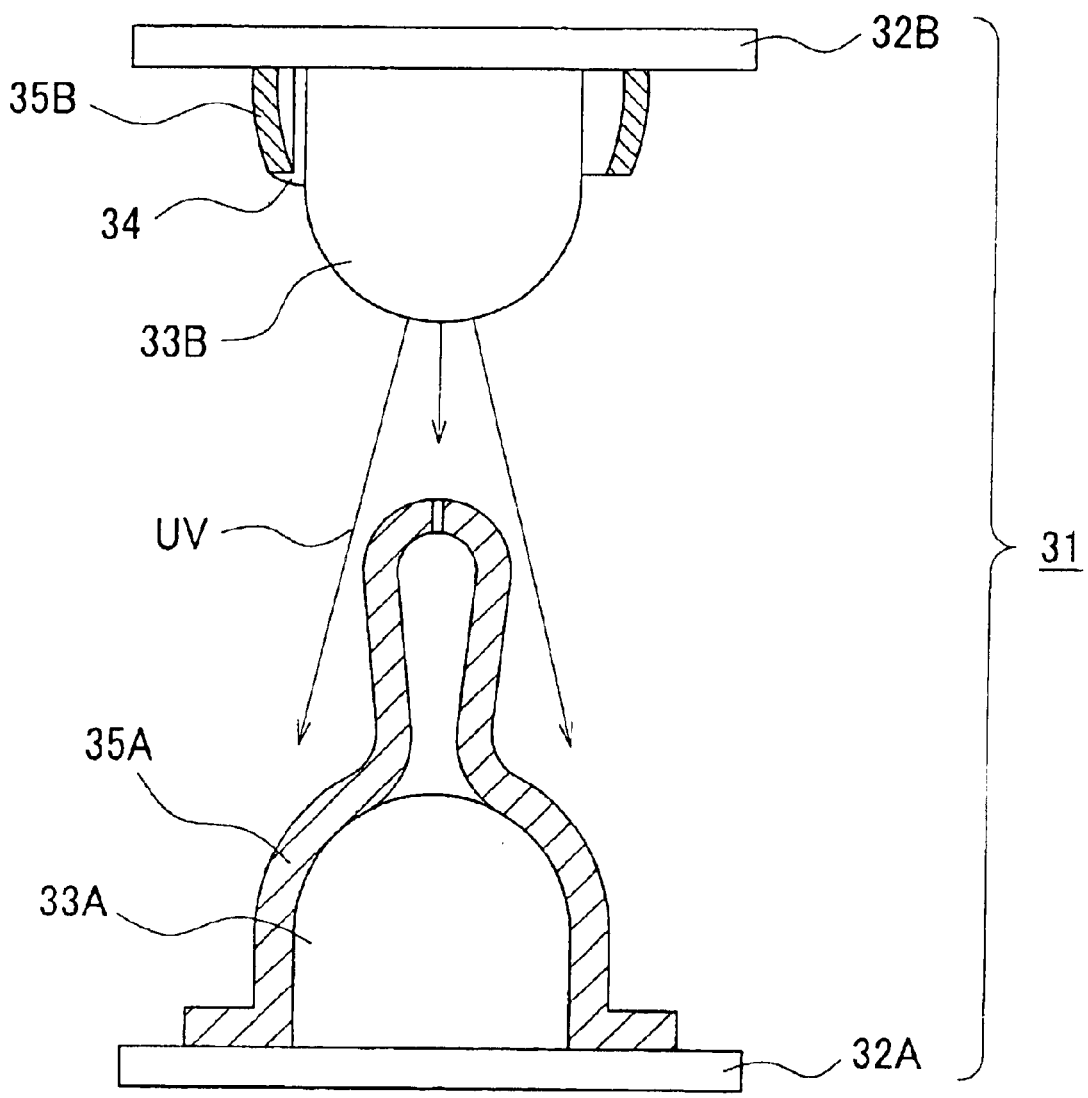
FIG. 12 is a sectional view showing a modification of the sterilizer in the fourth embodiment.

FIG. 12 is a sectional view showing a modification of the sterilizer 31 in the fourth embodiment. The second bulb 33B is fixed on a second holder 32B, and a ring shaped object 35B such as a screw of a baby's bottle is held by hooks 34 formed on the second holder 32B. For distinguishing from the second holder 32B, the holder on which the first bulb 33A is fixed is designated by numeral 32A, and the object (for example, a teat of the baby's bottle) which is laid over the first bulb 33A is designated by numeral 35A.

In the modification shown in FIG. 12, the second bulb 33B is formed the same as the first bulb 33A, and supported by the second holder 32B in a manner so that a peak portion of the second bulb 33B is protruded from an opening formed at the center of the (ring shaped) object 35B. By such a configuration, the ultraviolet rays are irradiated to the object 35A from the peak portion of the second bulb 33B protruded from the opening of the object 35B, so that the outer faces of the object 35A are sterilized owing to the ultraviolet rays. Furthermore, the ultraviolet rays are emitted from a portion of the second bulb 33B covered by the object 35B so as to irradiate the inner faces of the object 35B. As a result, the inner faces of the object 35B can be sterilized owing to the ultraviolet rays, so that a plurality of objects, for example, the teat and the screw of the baby's bottle can be sterilized simultaneously.

Fifth Embodiment

Figure 13:
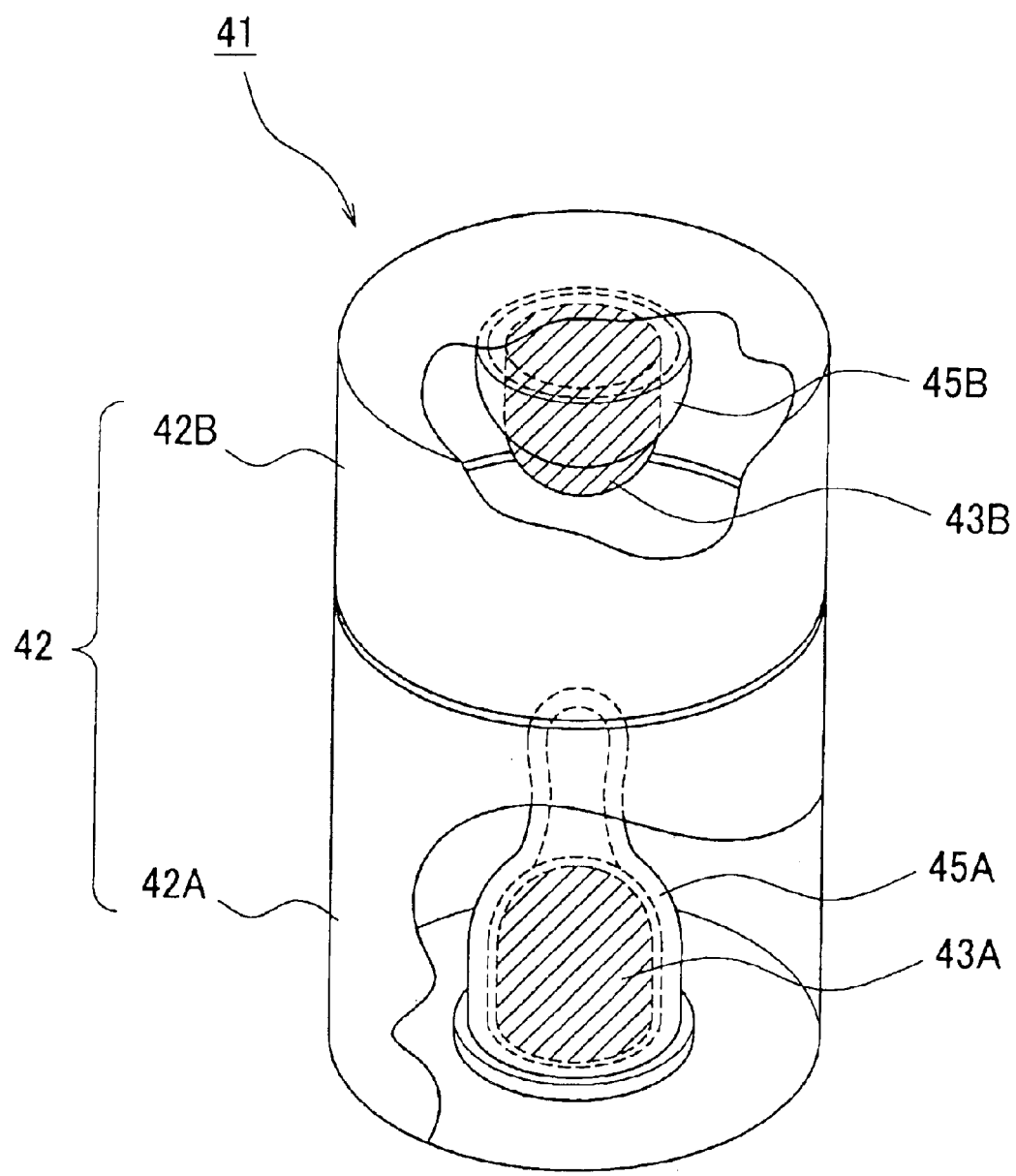
FIG. 13 is a perspective view showing a configuration of a sterilizer in a fifth embodiment of the present invention.
Figure 14:
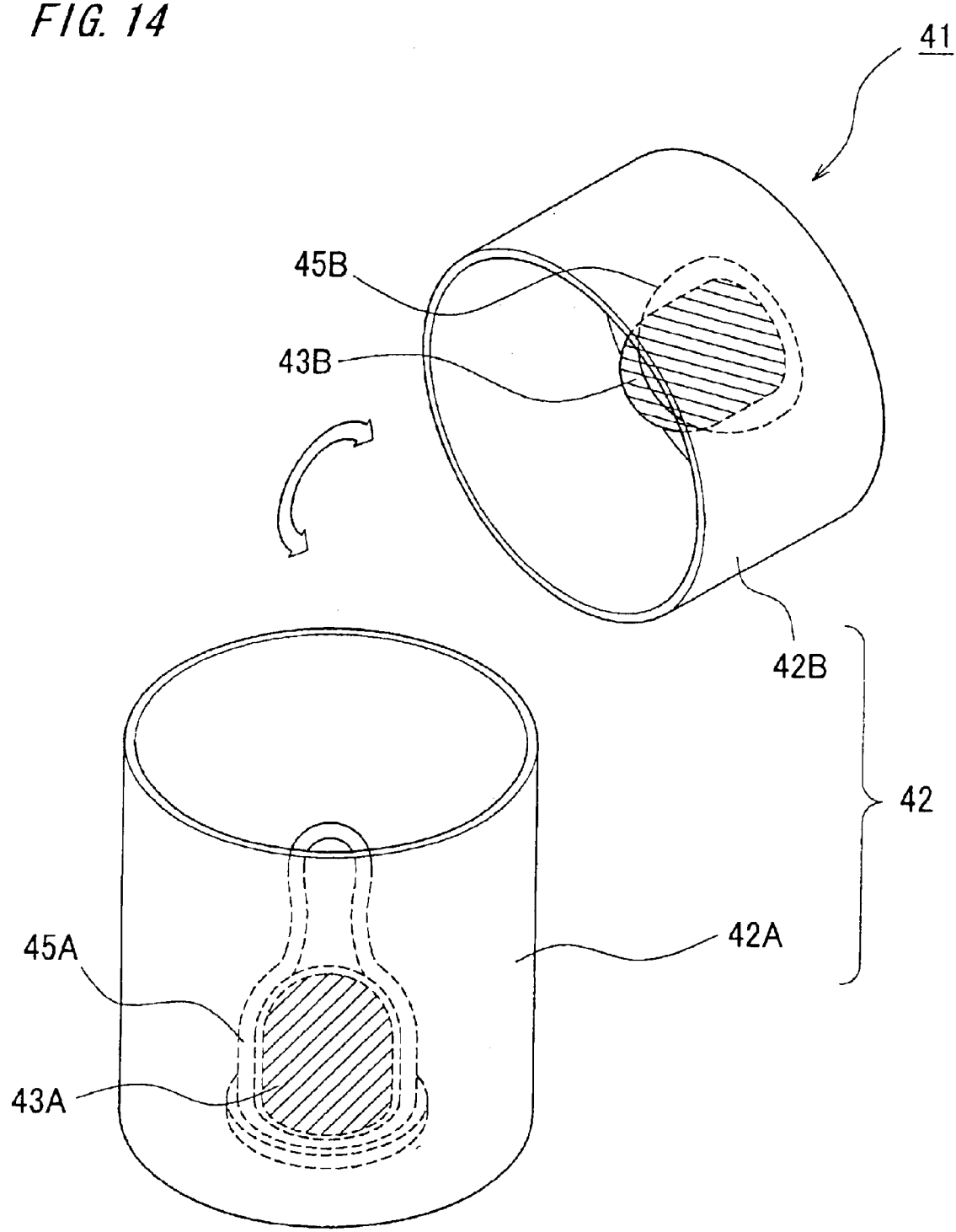
FIG. 14 is a perspective view showing a condition that a container of the sterilizer shown in FIG. 13 is opened.

A fifth embodiment of the present invention is described. FIG. 13 is a perspective view showing a configuration of a sterilizer 41 in the fifth embodiment. FIG. 14 is a perspective view showing a condition that a container 42 is opened.

The sterilizer 41 is constituted by a base member 42A and a cover member 42B constituting a tubular container 42, a first bulb 43A fixed on a bottom of the base member 42A, a second bulb 43B fixed on a ceiling of the cover member 42B, and so on. Hooks (not shown in the figure), which are similar to the hooks 34 in FIG. 12, are formed on the ceiling of the cover member 42B, so that a ring shaped object 45B such as the screw of the baby's bottle is held by the hooks. Furthermore, an object 45A such as the teat of the baby's bottle is directly laid over the first bulb 43A on the bottom of the base member 42A. Then, the cover member 42D is engaged with the base member 42A so as to seal the container 42, and the sterilizer 41 is put into an inside of a microwave oven (not shown in the figure) so that the microwaves are irradiated.

The base member 42A and the cover member 42B constituting the container 42 are respectively made of a material such as a fluoroplastic which transmits the microwave but the ultraviolet rays. Furthermore, it is preferable that at least the cover member 42B can transmit visible rays. Still furthermore, it is preferable that a fluorescent material is spread on at least a part of inner faces or outer faces of the base member 42A and the cover member 42B or the fluorescent material is mixed into the material of the base member 42A and the cover member 42B.

Further to the effect owing to the above-mentioned fourth embodiment, the sterilizer 41 in the fifth embodiment has an effect owing to the sealed container 42, that is, a serialization effect owing to ozone gas which is generated by the ultraviolet rays emitted from the first bulb 43A and the second bulb 43B. Furthermore, since the visible rays are generated by irradiation of the ultraviolet rays to the fluorescent material, a user can recognize the serialization owing to the ultraviolet rays has been processed from the visible rays transmitted through the container 42.

Figure 15:
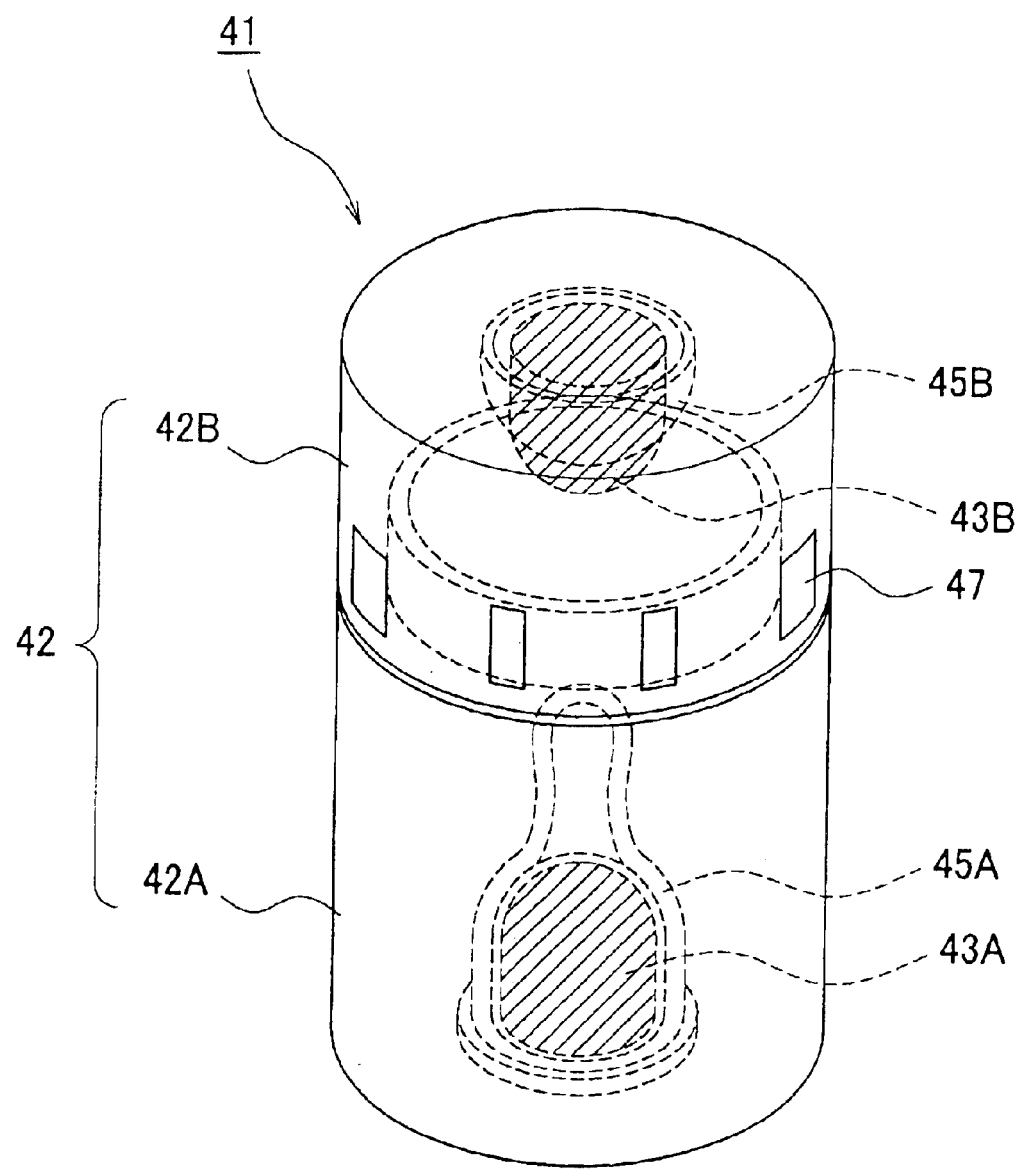
FIG. 15 is a perspective view showing a modification of the sterilizer in the fifth embodiment.
Figure 16:
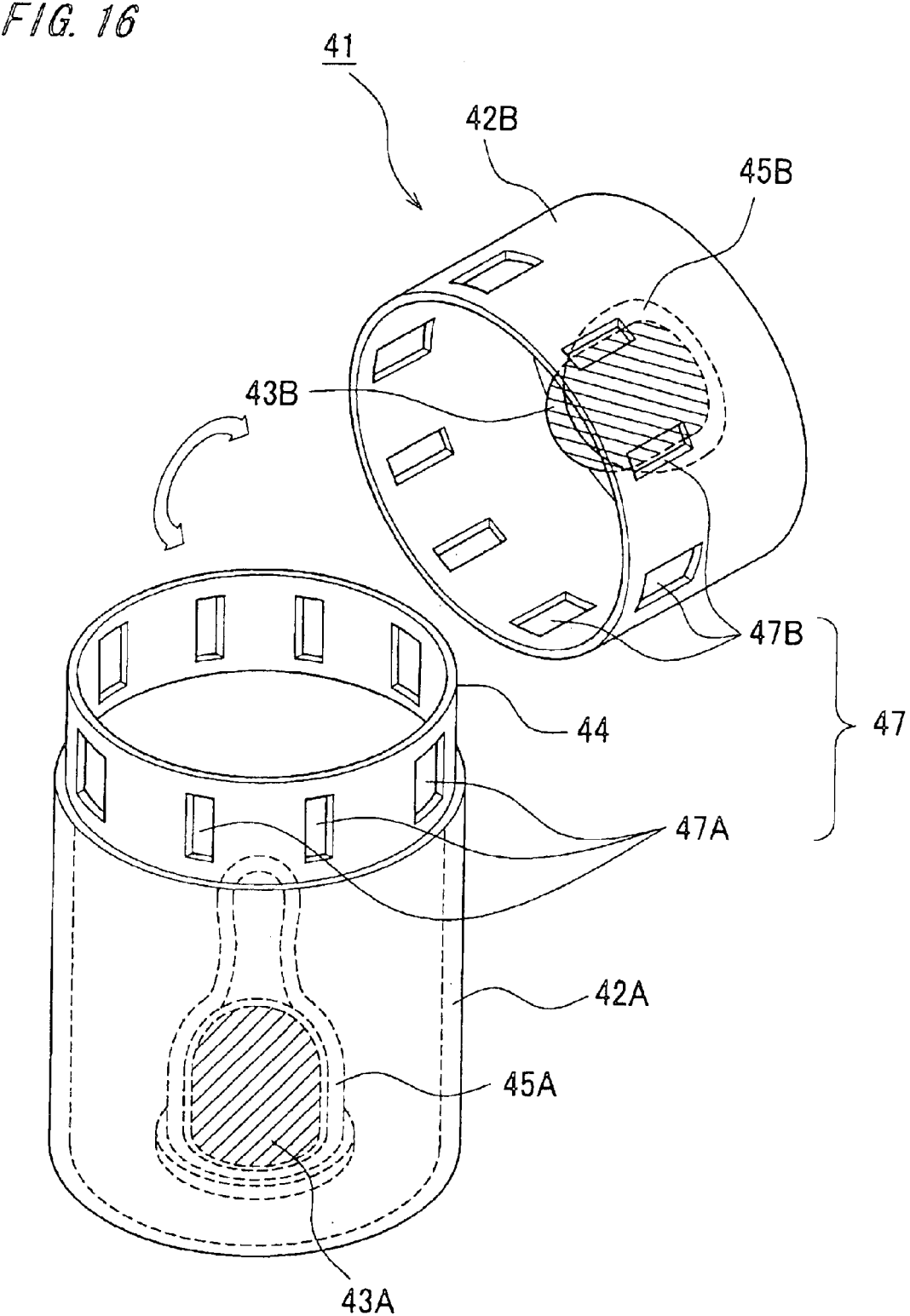
FIG. 16 is a perspective view showing a condition that a container of the sterilizer in the modification shown in FIG. 15 is opened.

A modification of the fifth embodiment is shown in FIGS. 15 and 16. FIG. 15 is a perspective view showing a modification of the sterilizer 41 in the fifth embodiment. FIG. 16 is a perspective view showing a condition that a container 42 is opened. In this modification, openable ventilation openings 47 are formed on the container 42.

As shown in FIG. 16, an offset portion 44, which is fitted to an inner periphery of the cover member 42B, is formed at an upper end of the base member 42A, and a plurality of openings 47A is formed on the offset portion 44 at a predetermined angle. Similarly, a plurality of openings 47B is formed in the vicinity of a lower end of the cover member 42B. Under a condition that the cover member 42B is engaged with the offset portion 44 of the base member 42A, the cover member 42B is rotatable with respect to the base member 42A, so that it can take a condition that the openings 47A and the openings 47B are completely overlapped, a condition that the openings 47A and the openings 47B are partially overlapped, and a condition that the openings 47A and the openings 47B are not overlapped. That is, open and close, and area of the openings of the ventilation openings 47 can be adjusted.

By such a configuration, the sterilizer can be used as follows. For example, when the microwaves are irradiated while the ventilation openings 47 are opened, the ultraviolet rays are emitted from the first bulb 43A and the second bulb 43B, and the objects 45A and 45B are sterilized owing to not only the ultraviolet rays but also the ozone gas generated by the irradiation of the ultraviolet rays. Furthermore, the ozone gas is released to the outside of the container 42 through the ventilation openings 47, so that the outside of the container 42 and the inside of the microwave oven can be sterilized by the ozone gas. Still furthermore, it is possible to prevent the adhesion of smell of ozone gas to the inside of the container 42, especially to the objects 45A and 45B by releasing the ozone gas to the outside of the container 42.

Sixth Embodiment

Figure 17:
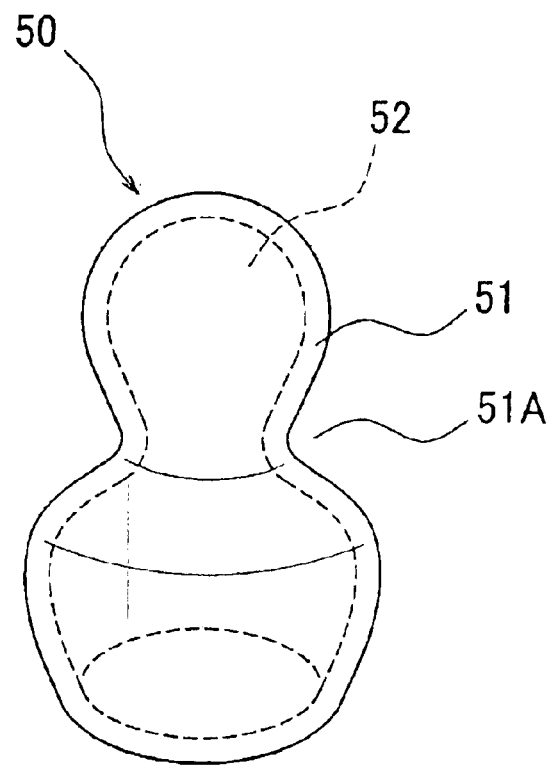
FIG. 17 is a perspective view showing a configuration of a bulb in a sixth embodiment of the present invention.
Figure 18:
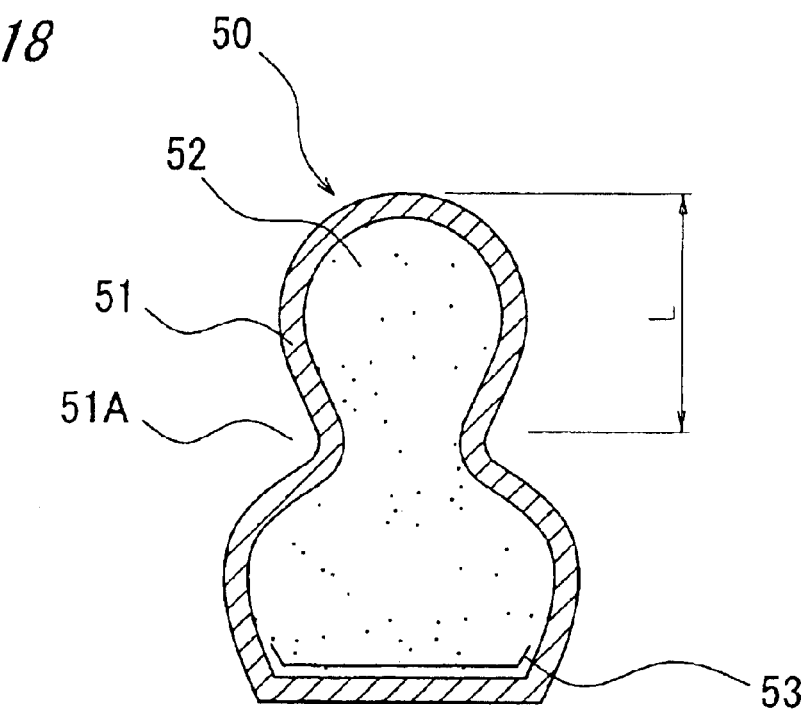
FIG. 18 is a sectional view of the bulb shown in FIG. 17.

A sixth embodiment of the present invention is described. The sixth embodiment relates to an electrodeless discharge bulb. FIG. 17 is a perspective view showing a configuration of a bulb 50 in the sixth embodiment. FIG. 18 is a sectional view thereof.

In the second to fifth embodiments, the bell shaped bulbs are used, respectively. In the bulb 50 in the sixth embodiment, a narrower diameter portion 51A in which an inner diameter and an outer diameter are made narrower than other portions is formed in a vicinity of the center in the height. The bulb 50 is configured by a midair member 51 in which at least a portion, preferably, whole except a bottom portion is made of a material transmitting the microwaves and the ultraviolet rays, and a material 52 emitting the ultraviolet rays enclosed in the midair member 51.

Mercury, deuterium, sulfur or the like, which emits ultraviolet rays by discharge electricity owing to ionization when it receives electric field energy of the microwaves, and maintains the discharge state, or owing to excitation by electric field energy of the microwaves, can be used independently, or concomitantly with another material as the material 52 emitting the ultraviolet rays.

When mercury is used as the material 52 emitting the ultraviolet rays, a capacity of the midair member 51 and a quantity of mercury are selected in a manner so that a pressure of mercury vapor in the inside of the midair member 51 becomes $1.33 \times 10^{-1}$ to 1.33 Pa ($1 \times 10^{-3}$ to $1 \times 10^{-2}$ Torr) during the irradiation of the microwaves (discharge electricity). That is, the ultraviolet rays can effectively be emitted from a few quantity of mercury by adjusting the quantity of mercury so as to make all of mercury in the inside of the midair member 51 is evaporated and the pressure of mercury vapor be $1 \times 10^{-3}$ to $1 \times 10^{-2}$ Torr while the ultraviolet rays are emitted by irradiating the microwaves to the bulb 50. Alternatively, when the material 52 emitting the ultraviolet rays includes deuterium, it is preferable that the pressure of deuterium is equal to or less than $34 \times 133$ Pa (34 Torr) at 25° C.

Subsequently, the reason of providing the narrower diameter portion 51A at substantially the center in height of the midair member 51 is described.

When the microwaves are irradiated to the bulb 50 and the ultraviolet rays are emitted from mercury molecules in the inside of the bulb 50, a part of the ultraviolet rays collides with and is absorbed by the mercury molecules floating in the inside of the bulb 50. The mercury molecules absorbing the ultraviolet rays are activated, and the temperature in the inside of the bulb 50 is increased. When the temperature is increased, the motion of the mercury molecules becomes intensive, so that the probability of collision with the ultraviolet rays becomes higher, and the probability of the absorption of the ultraviolet rays also becomes higher.

In a temperature region in which the increase of quantity the ultraviolet rays corresponding to the activation of the mercury molecules is larger than the increase of quantity of the absorption of the ultraviolet rays, the quantity of the ultraviolet rays increases corresponding to the increase of the temperature. However, when the temperature becomes higher than a turnoff temperature, the increase of quantity of the absorption of the ultraviolet rays overtakes the increase of quantity of the emission of the ultraviolet rays, so that the decrease of quantity of the ultraviolet rays occurs. Thus, a portion (coldest point) in which the temperature is lower than that in the another portion is provided in the inside of the bulb 50, and the temperature thereof is selected near to the turnoff temperature at which the quantity of the ultraviolet rays becomes the largest. The ultraviolet rays of wavelength 254 nm, which is effective to the serialization, has a higher absorption factor, so that the turnoff temperature thereof is lower about 42° C.

When the coldest point is provided in the bulb 50, the temperature at any portion except the coldest point is higher than the temperature at the coldest point, so that the kinetic energy of the mercury molecules is higher but the density of the molecules is lower. On the other hand, the kinetic energy of the mercury molecules is lower but the density of the molecules is higher in the vicinity of the coldest point. Thus, the ultraviolet rays can effectively be emitted at the temperature near to the turnoff temperature in the vicinity of the coldest point. Since the density of the mercury molecules lower at the portions except the coldest point, the probability of absorption of the ultraviolet rays is decreased. Therefore, the bulb 50 becomes similar to a condition that the ultraviolet rays are emitted at the temperature near to the turnoff temperature entirely, so that the quantity of the ultraviolet rays emitted from the bulb 50 can be maintained.

Behaviors after emitting the ultraviolet rays owing to irradiation of the microwaves are as mentioned above. It, however, is considered that mercury molecules are evenly distributed in the inside of the midair member 51 of the bulb 50 before starting the irradiation of the microwaves. Since the narrower diameter portion 51A in which the outer diameter and the inner diameter are narrower than those in another portion is provided on the midair member 51, the quantity of mercury molecules distributed in the vicinity of the narrower diameter portion 51A at the start is fewer than the quantity of mercury molecules distributed in another potion. Thus, when the irradiation of the microwaves is started, a total energy that the mercury molecules in the vicinity of the narrower diameter portion 51A receive is smaller than a total energy that the mercury molecules in another portion receive, so that a calorific power in the vicinity of the narrower diameter portion 51A is smaller. Accordingly, even when the emission of the ultraviolet rays from the mercury molecules is started corresponding to start the irradiation of the microwaves, the increase of the temperature in the vicinity of the narrower diameter portion 51A is slower than the increase of the temperature in another portion in the midair member 51, so that the temperature in the vicinity of the narrower diameter portion 51A is always lower than the temperature in another portion, and it becomes the coldest point in the bulb 50. By shaping the midair member 51 in a manner so that the calorific power from the vicinity of the narrower diameter portion 51A and the radiation power from the surface of the midair member 51 in the vicinity of the narrower diameter portion 51A are balanced at a temperature near to the turnoff temperature, it is possible to continue the emission of the ultraviolet rays effectively and stably over the long term.

Since the position of the narrower diameter portion 51A serving as the coldest point of the bulb 50 is not necessarily positioned in the vicinity of the center in height, it is needless to say that the coldest point can be provided at another portion. Furthermore, since the temperature at the coldest point is not necessarily coincided with the turnoff temperature of the ultraviolet rays, it is sufficient that the temperature at the coldest point is near to the turnoff temperature. For example, when the ultraviolet rays have the wavelength of 254 nm as mentioned above, it is sufficient that the temperature at the coldest point is equal to or less than 50° C. Furthermore, since the midair member of the bulb 50 has not necessarily the narrower diameter portion 51A as illustrated in the figure, it is sufficient that a portion having a smaller sectional area than that of another portion is formed on at least a part of the inner face. When a protrusion is formed on the inner face of the midair member instead of the narrower diameter portion 51A, the same effect can be obtained.

As shown in FIG. 18, an adminicle member 53 made of a metal foil such as an aluminum foil is further provided in the vicinity of the bottom portion in the inside of the midair member 51. Since the adminicle member 53 absorbs the energy of the microwaves and generates heat, the temperature in circumferences of the adminicle member 53 is increased so that mercury becomes evaporable. Therefore, the ultraviolet rays can stably be emitted immediately from the start of the irradiation of the microwaves.

Furthermore, it is preferable that the height of the bulb 50 (or the length of the longest portion of the midair member 51) is substantially equal to at least a half length "L" of the wavelength of the microwaves or an integral multiple thereof. The length "L" will be varied corresponding to the wavelength of the microwaves actually used. For example, when the wavelength of the microwaves is 12 cm, the half length "L" of the wavelength becomes 6 cm, so that the height of the bulb 50 (or the length of the longest portion of the midair member 51) is selected to be about 6 cm (60 mm).

That is, since the bulb 50 can be regarded as an antenna with respect to the microwaves, when the antenna has a length corresponding to a half length of the wavelength of radio waves to be received, both ends of the antenna correspond to node of wave, and the center of the antenna corresponds to the antinode, so that the resonance of waves occurs, and the microwaves are effectively absorbed. Thus, the energy of the microwaves can effectively be absorbed and the quantity of the ultraviolet rays can be increased. Since the bulb having the height or length of 60 mm is a fair size, it is suitable for sterilizing the object having a large size or a large area, or suitable for sterilizing a plurality of objects simultaneously.

Seventh Embodiment

Figure 19:
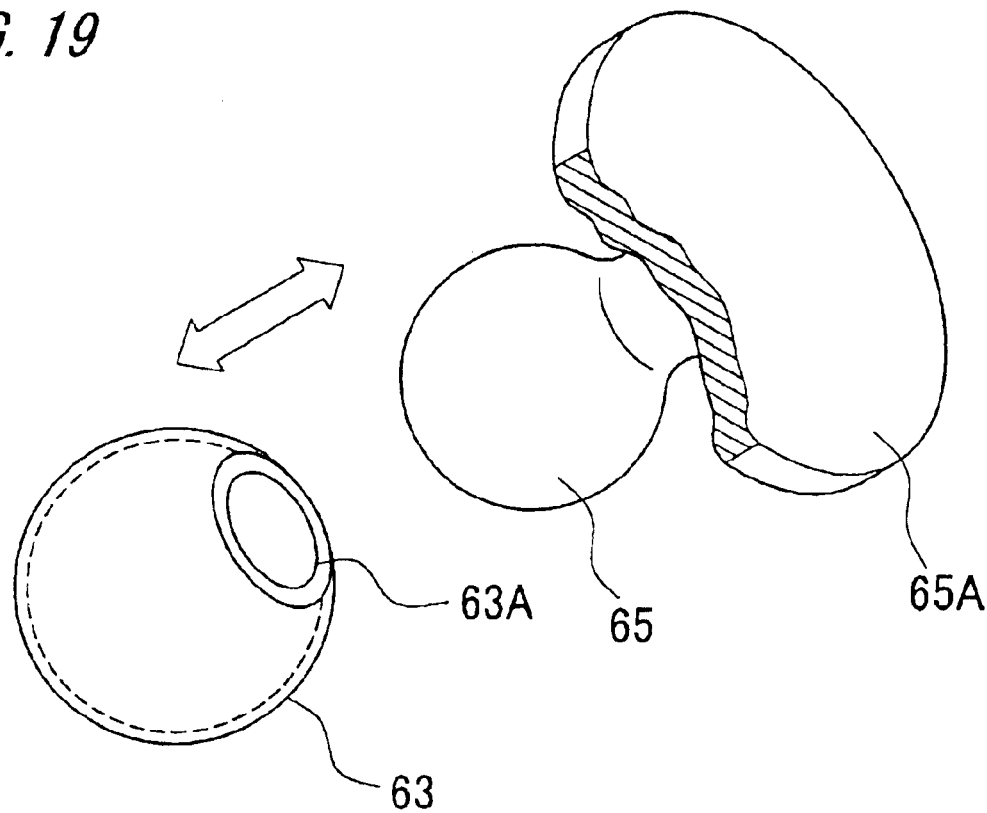
FIG. 19 is a perspective view showing shapes of a bulb and an object to be sterilized in a seventh embodiment of the present invention.
Figure 20:
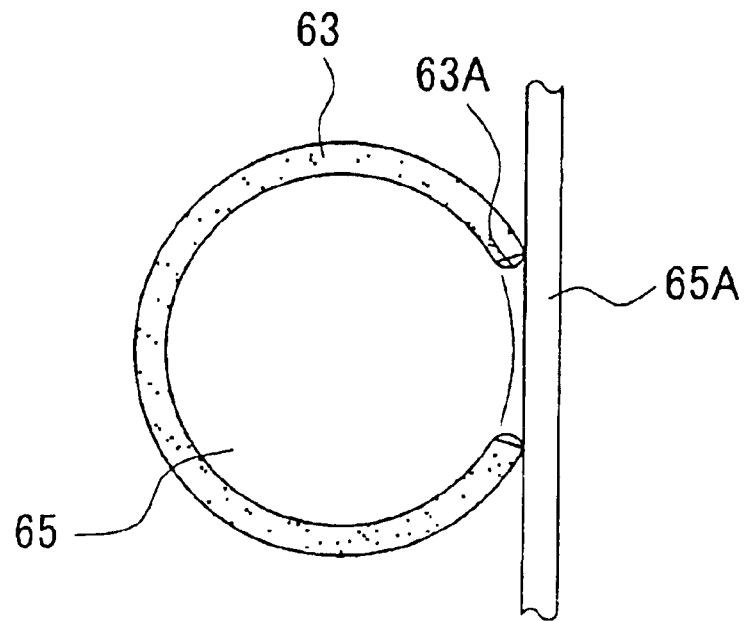
FIG. 20 is a sectional view showing a condition that the object is fitted into the bulb in the seventh embodiment.

A seventh embodiment of the present invention is described. In the above-mentioned first to sixth embodiments, the objects (for example, the teat and the screw of the baby's bottle, and so on) are laid over the bulb so as to be sterilized. In the seventh embodiment, an objective portion of an object to be sterilized is fitted into a hollow portion of a bulb so as to be sterilized. FIG. 19 is a perspective view showing shapes of a bulb 63 and an object 65 in the seventh embodiment. FIG. 20 is a sectional view showing a condition that the object 65 is fitted into the bulb 63.

The object 65 having flexibility is, for example, a pacifier which is to be put into baby's mouth. The bulb 63 has a hollow portion having substantially the same shape and dimension as but a little larger than the shape and the dimension of the objective portion to be sterilized of the object 65. Since an opening 63A of the bulb 63 is smaller than the largest diameter of the hollow portion, the elastic deformation of the object 65 is utilized for fitting the object 65 into the hollow portion of the bulb 63 and for taking the object 65 from the hollow portion after the serialization procedure. The numeral 65A designates a collar for preventing catch on of the pacifier.

The bulb 63 is substantially a sphere inside of which is formed hollow, and a wall portion constituting the sphere is further made midair into which mercury vapor is enclosed. Alternatively, it is possible that the wall portion is not formed midair, and a material such as sulfur emitting the ultraviolet rays owing to receiving electric field energy of the microwaves is mixed in a material forming the wall portion.

As mentioned above, by shaping an ultraviolet ray emitting face of the bulb 63 substantially the same as the shape of the objective portion of the object 65 and they are tightly contacted with each other, the objective portion of the object 65 can be sterilized evenly without omission.

Since the exterior of the bulb 63 is not restricted to the sphere, it is possible to have a tubular shape, a cuboid, or the like. Furthermore, since the shape of the objective portion of the object 65 is not restricted by the sphere, it is possible to have a spindle shape or another shape.

Contrary to the above-mentioned configuration, when the object to be sterilized is substantially a sphere with hollow portion and made of an elastic material such as a rubber, it is possible to constitute that the bulb is formed as a midair sphere and the object is laid over the outside of the bulb with utilizing the elasticity of the object.

Eighth Embodiment

Figure 21:
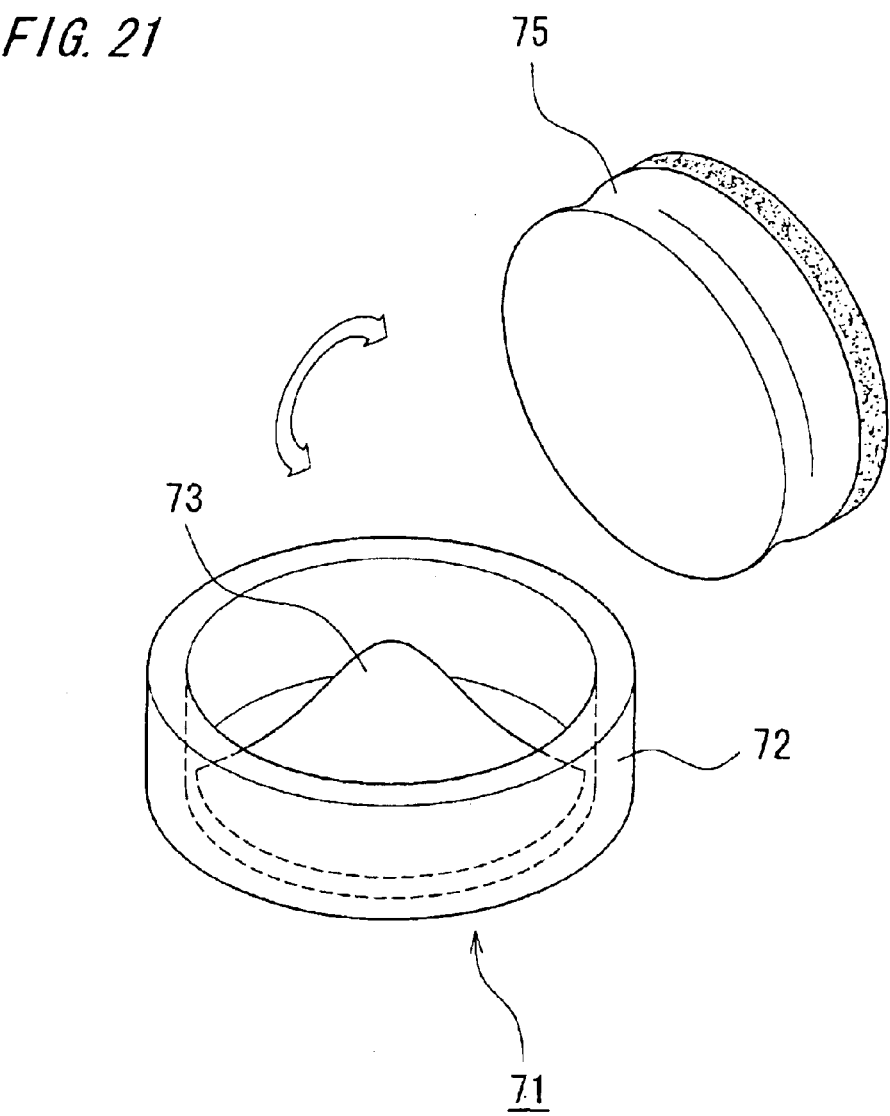
FIG. 21 is a perspective view showing shapes of a sterilizer and an object to be sterilized in an eighth embodiment of the present invention.
Figure 22:
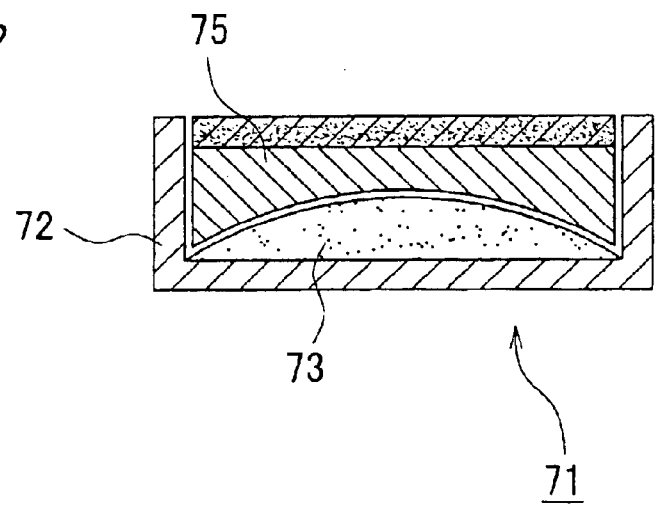
FIG. 22 is a sectional view showing a condition that the object is disposed on the sterilizer in the eighth embodiment.

An eighth embodiment of the present invention is described. In the eighth embodiment, an object is tightly disposed on a bulb so as to be sterilized. FIG. 21 is a perspective view showing shapes of a sterilizer 71 and an object 75 in the eighth embodiment. FIG. 22 is a sectional view showing a condition that the object 75 is disposed on the sterilizer 71. A sponge for washing dishes is illustrated as an example of the object 75.

The sterilizer 71 is configured by a tray 72 having, for example, a circular shape, an elliptic shape, a pill shape, a rectangular shape or the like, and a bulb 73 fixed on a bottom of the tray 72 and formed convex curve at the center portion. The bulb 73 is, for example, a midair member made of a glass, and mercury vapor or the like is enclosed therein.

Since the object 75 is an elastic member such as the above-mentioned sponge, it is preferable that the object 75 is elastically deformed so that the bottom of the object 75 is tightly contacted with the surface of the bulb 73 by applying the pressure from above, under a condition that the object 75 is disposed on the bulb 73 of the tray 72. Therefore, it is possible to use a cap, which is not illustrated, for pressing the object 75 to the bulb 73 from above the tray 72.

By such the eighth embodiment, since the bulb 73 and the object 75 are tightly contacted, a relative positional relationship between the bulb 73 and the object 75 is not varied and the serialization can be processed stably, even when vibrations owing to rotation of a table are applied while they are put into an inside of a microwave oven for being irradiated the microwaves so as to sterilize the object.

Ninth Embodiment

Figure 23:
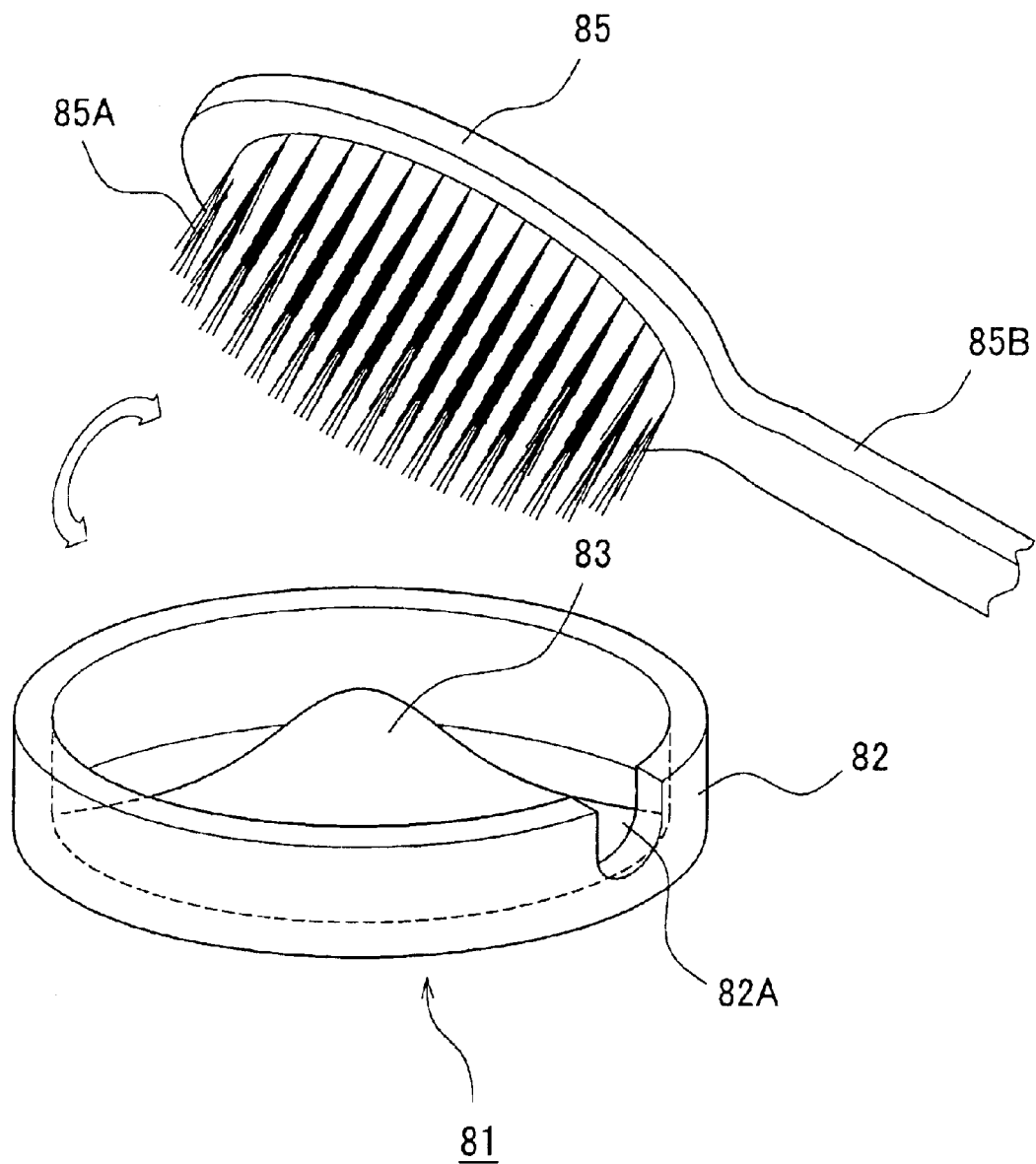
FIG. 23 is a perspective view showing shapes of a sterilizer and an object to be sterilized in a ninth embodiment of the present invention.
Figure 24:
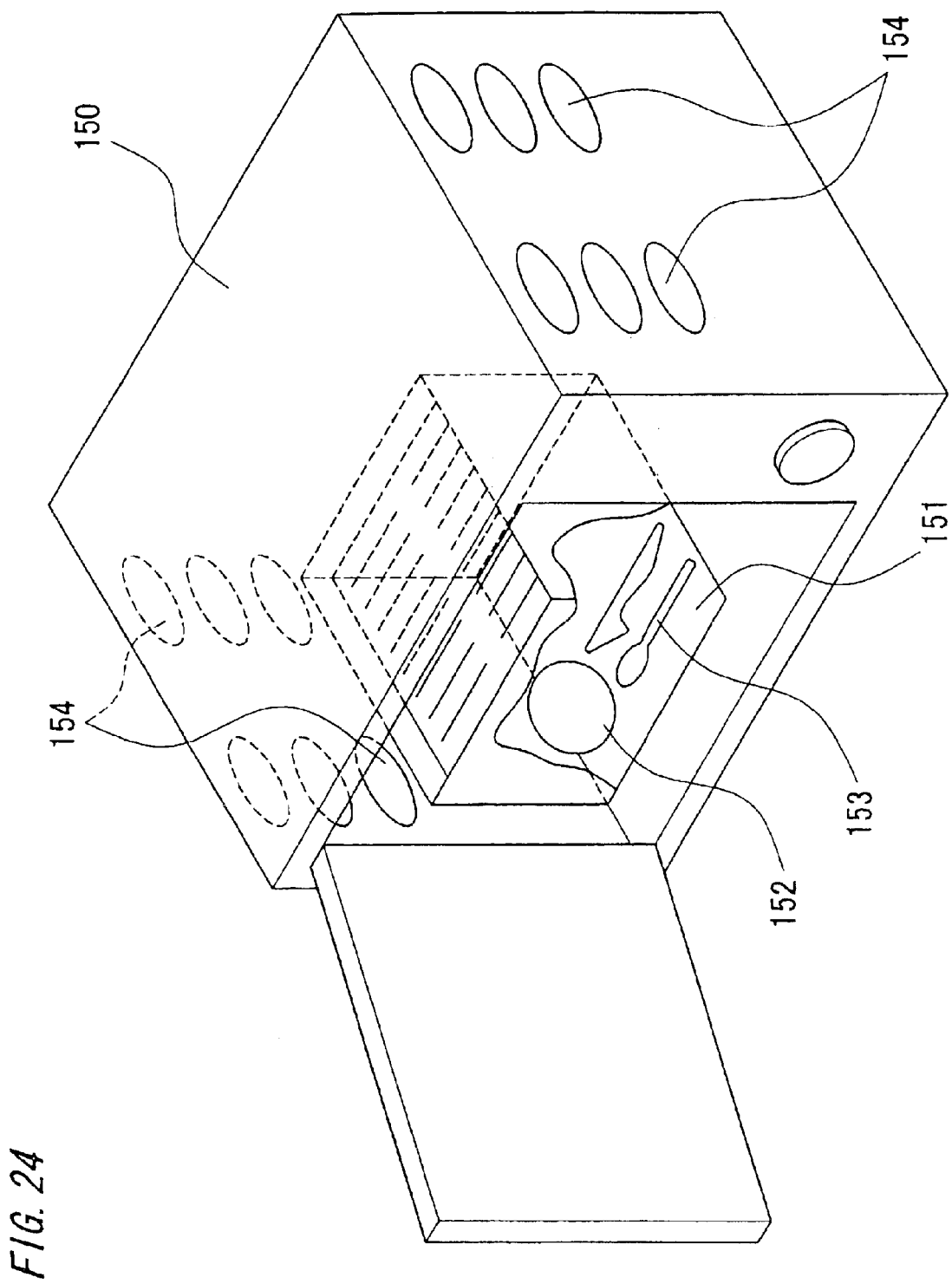
FIG. 24 is the perspective view showing the sterilizing method for medical implements according to the first prior art.
Figure 25:
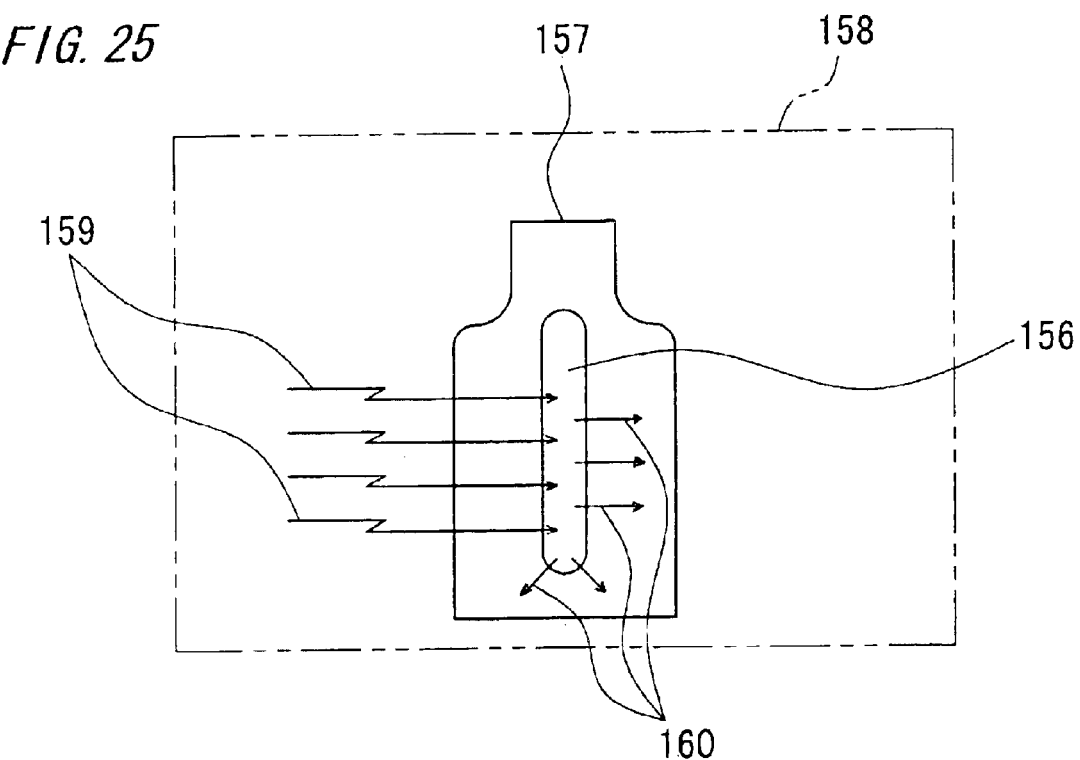
FIG. 25 is the side view showing the sterilizing method of the container such as the glass bottle according to the second prior art.
Figure 26:
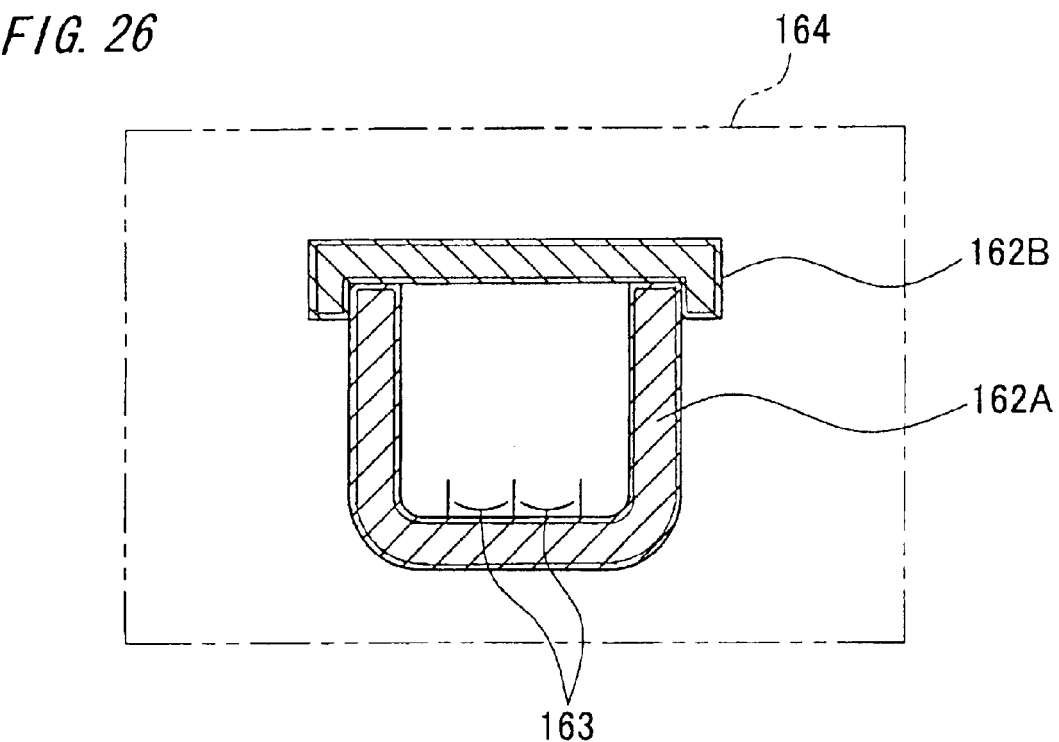
FIG. 26 is the sectional view showing the sterilizing method of the contact lenses according to the third prior art.

A ninth embodiment of the present invention is described. In the ninth embodiment, an object is tightly disposed on a bulb so as to be sterilized, similar to the eighth embodiment. FIG. 23 is a perspective view showing shapes of a sterilizer 81 and an object 85 to be sterilized in the ninth embodiment. A toothbrush is illustrated as an example of the object 85.

The sterilizer 81 is configured by a tray 82 having, for example, a circular shape, an elliptic shape, a pill shape or the like, and a bulb 83 fixed on a bottom of the tray 82 and formed convex curve at the center portion. The bulb 83 is, for example, a midair member made of a glass, and mercury vapor or the like is enclosed therein. A cutting 82A, to which a handgrip 85B of the object (toothbrush) 85 is fitted, is formed on a perpendicular wall portion of the tray 82.

Since the object 85 is the toothbrush as mentioned above, when the handgrip 85B of the toothbrush 85 is fitted to the cutting 82A of the tray 82 under the condition that the object 85 is disposed on the bulb 83 of the tray 82, a brush portion 85A is elastically deformed, so that top ends of the brush portion 85A are tightly contacted with a surface of the bulb 83. It is possible to use a cover (not shown in the figure) for sealing the brush portion 85A of the object 85. In the latter case, the serialization owing to ozone gas generated corresponding to the emission of the ultraviolet rays can be processed simultaneously. Furthermore, since a toothbrush, in which lengths of the brush portion are periodically varied so as to follow the convex and concave of the teeth, is known, it is possible to provide periodical convex and concave on the surface of the bulb 83.

By such the ninth embodiment, since the bulb 83 and the brush portion 85A which is the objective portion to be sterilized of the object 85 are tightly contacted, a relative positional relationship between the bulb 83 and the object 85 is not varied and the serialization can be processed stably, even when vibrations owing to the rotation of a table are applied while they are put into an inside of a microwave oven for irradiating the microwaves so as to sterilize the object.

Other Applications

In the above-mentioned description of the embodiments, it is described that the microwave oven for home use is used as the microwave generator. The present invention, however, is not restricted by the description. It is possible to prepare an exclusive microwave generator for business use. Since the objects to be sterilized are not restricted by the teat and screw of the baby's bottle, the pacifier, the toothbrush, the sponge for washing the dishes, it is possible to apply every thing which can be sterilized owing to the ultraviolet rays such as a main body of the baby's bottle, a returnable container, and so on.

As can be seen from the above-mentioned description of the embodiments, by contacting at least a part of the object to be sterilized with the bulb, the ultraviolet rays emitted from the bulb are directly irradiated to at least the contacting portion of the objective face of the object, so that the serialization owing to the ultraviolet rays can effectively be processed.

Furthermore, by forming at least a part of the bulb so as to have a shape following along the objective face of the object, the portion where the shape of the bulb and the objective face of the object face with each other serves as a guide. Thus, the distance between the bulb and the objective face is not varied and becomes substantially constant even when vibrations are applied from the outside, so that the serialization of the object can be processed stably.

Still furthermore, when the adminicle bulb having substantially the same configuration of the bulb is comprised, and the bulb and the adminicle bulb are respectively disposed so as to irradiate the ultraviolet rays toward a plurality of objective faces of the object, a plurality of the objective faces, for example, the inner face and the outer face of the same object can be sterilized simultaneously.

Still furthermore, when the bulb and the object to be sterilized are enclosed in the inside of the openable container, the object is further sterilized owing to ozone gas which is generated simultaneously when the ultraviolet rays are irradiated. If the container has not been opened, the ozone gas is sealed in the inside of the container while a predetermined term, so that the serialization owing to the ozone gas is maintained in a predetermined term.

Still furthermore, when the openable ventilation openings are provided on the container, the ozone gas generated by the irradiation of the ultraviolet rays can be released to the outside of the container by opening the ventilation openings, so that the smell due to the ozone gas can be removed. Furthermore, when the container is used under the condition that the ventilation openings are opened, the outside of the container can be sterilized by the ozone gas flown outwardly through the ventilation openings.

Still furthermore, when the container is formed by the material which transmits no ultraviolet ray, the ultraviolet rays is never leaked to the outside of the container. Thus, even when the user processes another operation in the circumference of the microwave oven while the serialization is processed, the ultraviolet rays rarely come into the user's eyes, so that the harm due to the ultraviolet rays can be prevented.

Still furthermore, when at least a part of the container is formed by the material which transmits visible rays, it is possible to observe the inside of the container during the serialization without the harm due to the ultraviolet rays, so that the serialization process can be confirmed.

Still furthermore, when the fluorescent material is spread on at least the inner face or the outer face of the container or when the fluorescent material is mixed into the material of the container, the visible rays can be emitted simultaneously with the ultraviolet rays, and the visible rays are transmitted to the outside of the container, so that the user can confirm the serialization owing to the ultraviolet rays by the visible rays. Still furthermore, it is possible to find the deterioration of the bulb from the reduction of the intensity of the visible rays.

Still furthermore, when the midair member of the bulb has the protrusion on the inner face or has the portion having the diameter smaller than that in another portion, the vicinity of the protrusion or the portion having the smaller diameter serves as the coldest point of the temperature in the bulb during the irradiation of the microwaves. Furthermore, when the temperature at the coldest point is selected to be equal to or less than 50° C., the ultraviolet rays can be emitted continuously and effectively.

Still furthermore, when the longest dimension among the dimensions of respective portions of the midair member is selected substantially equal to the half length of the wavelength of the microwaves or an integral multiple thereof, the energy of the microwaves can effectively be absorbed with utilizing the resonance of the microwaves so as to emit the ultraviolet rays.

Still furthermore, when the bulb has the adminicle member for subserving the activation of the discharge of the enclosed material owing to the microwaves, the temperature in the inside of the bulb is increased owing to the heat of the adminicle member absorbing the energy of the microwaves, so that the material such as mercury emitting the ultraviolet rays can be activated. Accordingly, the quantity of the ultraviolet rays just after starting the emission of the ultraviolet rays can be increased.

This application is based on Japanese patent application 2001-315237 filed in Japan, the contents of which are hereby incorporated by references.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be constructed as being included therein.

INDUSTRIAL APPLICABILITY

As mentioned above, the sterilizer in accordance with the present invention can process the serialization of the object owing to the ultraviolet rays with using the microwave generator such as the microwave oven for home use.

What is claimed is:

1. A sterilizer for sterilizing a surface of an object by irradiation of ultraviolet rays onto the surface, said sterilizer comprising:
    a first electrodeless discharge bulb fixed on one of a base member and a cover member, the first electrodeless discharge bulb containing a material that emits the ultraviolet rays when the material is irradiated by the microwaves; and
    a first holder provided on one of the base member and the cover member to hold the object so that the surface of the object faces an ultraviolet ray emitting face of the first electrodeless discharge bulb.

2. The sterilizer in accordance with claim 1, wherein at least a part of the bulb contacts the object.

3. The sterilizer in accordance with claim 1, wherein at least a part of the bulb has a shape that substantially follows a shape of the object.

4. The sterilizer in accordance with claim 1, further comprising a second electrodeless discharge bulb fixed on one of the base member and the cover member and having substantially a same configuration as a configuration of the first electrodeless discharge bulb, wherein the first electrodeless discharge bulb and the second electrodeless discharge bulb are respectively positioned to irradiate the ultraviolet rays to a plurality of surfaces of the object.

5. The sterilizer in accordance with claim 4, further comprising:
    a second holder formed on one of the base member and the cover member, wherein a second object having a surface and a portion transmitting the ultraviolet rays is held so that the surface of the second object faces the second electrodeless discharge bulb and the portion transmitting the ultraviolet rays is disposed between the second electrodeless discharge bulb and the object held on the first holder.

6. The sterilizer in accordance with claim 1, further comprising openable ventilization openings provided on one of the base member and the cover member.

7. The sterilizer in accordance with claim 1, wherein at least a part of the cover member and the base member comprise a material which transmits visible rays.

8. The sterilizer in accordance with claim 1, further comprising a fluorescent material emitting visible rays of the ultraviolet rays spread on one of an inner face and an outer face of the base member and the cover member, or the fluorescent material is mixed in a material of the base member and the cover member.

9. The sterilizer in accordance with claim 1, wherein the first electrodeless discharge bulb comprises a midair member which is electrodeless and airtight, and which transmits the ultraviolet rays from at least a part thereof, and a material which is enclosed in the midair member and emits ultraviolet rays by discharging when electric field energy of the microwaves is received.

10. The sterilizer in accordance with claim 9, wherein the enclosed material comprises a quantity of mercury such that a pressure of evaporated mercury becomes $1.33 \times 10^{-1}$ to $1.33$ Pa ($1 \times 10^{-3}$ to $1 \times 10^{-2}$ Torr) when the microwaves are irradiated.

11. The sterilizer in accordance with claim 10, wherein the enclosed material comprises a quantity of mercury that completely evaporates while the microwaves are irradiated.

12. The sterilizer in accordance with claim 10, wherein the enclosed material includes deuterium.

13. The sterilizer in accordance with claim 12, wherein a pressure of deuterium is equal to or smaller than $34 \times 133$ Pa ($34$ Torr) at a temperature of $25°$ C.

14. The sterilizer in accordance with claim 10, wherein the enclosed material includes sulfur.

15. The sterilizer in accordance with claim 9, wherein the midair member includes a protrusion on an inner face or includes a portion having a smaller diameter than another portion; and
    a vicinity of the protrusion or the portion having the smaller diameter is configured to include a lowest temperature of the bulb during irradiation of the microwaves;
    the lowest temperature being equal to or less than $50°$ C.

16. The sterilizer in accordance with claim 9, wherein a longest dimension of the midair member is substantially equal to a half length of a wavelength of the microwaves or an integral multiple thereof.

17. The sterilizer in accordance with claim 9, wherein the first electrodeless discharge bulb has an adminicle member for subserving activation of discharge of the enclosed material from the microwaves.

18. The sterilizer according to claim 1, wherein the cover member is supported by the base member, the cover member being attachable and detachable from the base member.

* * * * *

UNITED STATES PATENT AND TRADEMARK OFFICE
CERTIFICATE OF CORRECTION

PATENT NO. : 6,987,273 B1
APPLICATION NO. : 10/416505
DATED : January 17, 2006
INVENTOR(S) : S. Okuda et al.

Page 1 of 1

It is certified that error appears in the above-identified patent and that said Letters Patent is hereby corrected as shown below:

At column 16, line 28 (claim 12, line 1) of the printed patent, "claim 10" should be --claim 9--.

At column 16, line 33 (claim 14, line 1) of the printed patent, "claim 10" should be --claim 9--.

Signed and Sealed this

Twelfth Day of September, 2006

JON W. DUDAS
*Director of the United States Patent and Trademark Office*